US006984513B2

(12) United States Patent
Brown et al.

(10) Patent No.: US 6,984,513 B2
(45) Date of Patent: *Jan. 10, 2006

(54) ANAEROBE TARGETED ENZYME-MEDIATED PRODRUG THERAPY

(75) Inventors: John M. Brown, Redwood City, CA (US); Shie-Chau Liu, Redwood City, CA (US); Amato J. Giaccia, Stanford, CA (US); Nigel P. Minton, Salisbury (GB)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 80 days.

This patent is subject to a terminal disclaimer.

(21) Appl. No.: 10/158,976

(22) Filed: May 31, 2002

(65) Prior Publication Data

US 2003/0103952 A1 Jun. 5, 2003

Related U.S. Application Data

(63) Continuation-in-part of application No. 09/803,330, filed on Mar. 9, 2001, now abandoned, application No. 10/158,976, which is a continuation-in-part of application No. 10/151,069, filed on May 17, 2002, now Pat. No. 6,652,849, which is a continuation of application No. 08/686,502, filed on Jul. 23, 1996, now Pat. No. 6,416,754, which is a continuation of application No. 08/465,932, filed on Jun. 6, 1995, now abandoned, which is a continuation of application No. 08/227,313, filed on Apr. 13, 1994, now abandoned, which is a continuation of application No. 08/206,430, filed on Mar. 3, 1994, now abandoned.

(51) Int. Cl.
C12N 1/20 (2006.01)
A01N 63/00 (2006.01)

(52) U.S. Cl. .................................. 435/252.7; 424/93.41
(58) Field of Classification Search .............. 435/252.7; 424/93.41
See application file for complete search history.

(56) References Cited

U.S. PATENT DOCUMENTS

5,633,158 A 5/1997 Anlezark et al.
6,416,754 B1 * 7/2002 Brown et al. ............. 424/93.21
6,652,849 B2 * 11/2003 Brown et al. ............. 424/93.2

FOREIGN PATENT DOCUMENTS

DE 228301 10/1985
WO WO 93/08288 4/1993

OTHER PUBLICATIONS

Fox et al. Anaerobic bacteria as a delivery system for cancer gene therapy: in vitro activation of 5-fluorocytosine by genetically engineered clostridia Gene Therapy vol.3 pp. 173–178 1996 (cited by Applicant).*

Lemmon et al. Anaerobic bacteria as a gene delivery system that is controlled by the tumor microenvironment Gene Therapy vol. 4 pp. 791–796 1997 (cited by Applicant).*
Liu et al. Anticancer efficacy of systemically delivered anaerobic bacteria as gene therapy vectors targeting tumor hypoxia/necrosis Proceedings of the American Association for Cancer Research vol. 41 Mar. 2000 (cited by Applicant).*
Anlezark, et al., *Biochem. Pharmacol.* 44:2289–2295, (1992).
Antoniw, et al., *Br. J. Cancer* 62:909–914, (1990).
Bagshawe, *Br. J. Cancer* 60:275–281, (1989).
Boyd, *Current therapy in Oncology*, Decker et al., eds, pp. 11–22, (1992).
Bryant, et al., *J. Biol. Chem.* 266:4126–4130, (1991).
*Davis, T.O., et al., *J. Mol. Microbiol. Biotechnol.* 2(1):59–69, (2000).
Fitzgerald, et al., *Biochem. Soc. Trams.* 20:731–734, (1992).
**Fox, M.E., et al., *Gene Therapy* 3:173–178, (1996).
Graves, et al., *Proc. Natl. Acad. Sci. USA* 82:1653–1657, (1985).
*Hamstra, D.A., et al., *Human Gene Therapy* 10:1993–2003, (1999).
Jain, *J. Natl. Cancer Inst.* 81:570–576, (1989).
**Lemmon, M.J., et al., *Gene Therapy* 4:791–796, (1997).
**Liu, et al., *Proceedings of the American Association Cancer Research* 41:733–734, (Mar. 2000).
*Liu, S.C., et al., *Gene Therapy* 9:291–296, (2002).
*Melton, R.G. and Sherwood, R.F., *J. Natl. Cancer Inst.* 88(3/4):153–165, (1996).
*Minton, N.P., et al., *FEMS Microbiol. Lett.* 17:357–364, (1995).
Mullen et al, *Proc. Natl. Acad. Sci. USA* 89:33–37, (1992).
*Niculescu–Duvaz, et al., *Anti–Cancer Drug Design* 14:517–538, (1999).
Oultram, et al., *FEMS Microbiol. Lett.* 56:83–88, (1988).
Rosenberg, *JAMA* 268:2416–2419, (1992).
Schlechte, et al., *Zbl. Bakt. Hyg. A268*:347–356, (1988).
Senter, *FASEB J.* 4:188–193, (1990).
Thiele, et al., *Cancer Res.* 24:234–238, (1964).
Watanabe, et al., *Nucleic Acid Res.* 18:1059, (1990).

* cited by examiner

*Primary Examiner*—James Ketter
*Assistant Examiner*—Konstantina Katcheves
(74) *Attorney, Agent, or Firm*—Perkins Coie LLP

(57) ABSTRACT

Recombinant anaerobic bacterial compositions that under anaerobic conditions present in a solid tumor and produce an enzyme capable of catalyzing the conversion of a prodrug to its cytotoxic product in situ are described. Methods of treating tumors using the composition are also described.

26 Claims, 12 Drawing Sheets

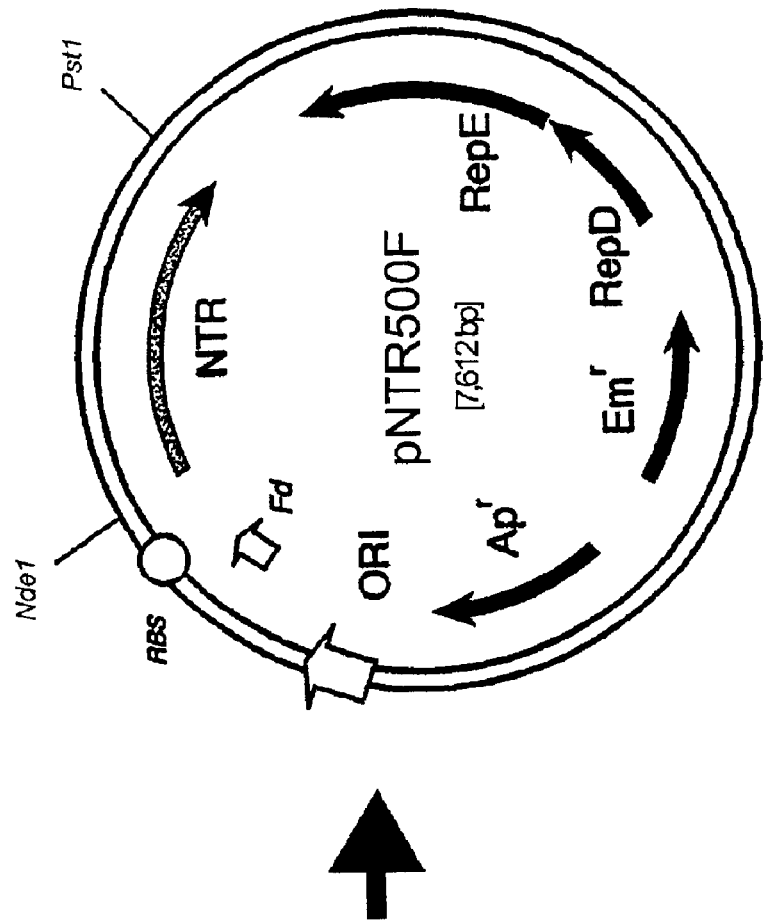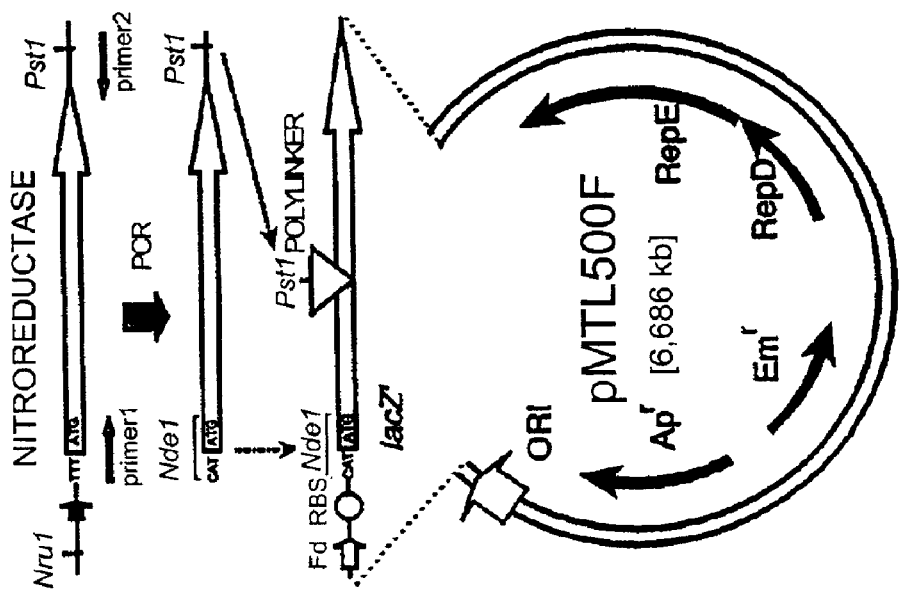
Fig. 1

```
            MboI
            ┌──┐
GAATTCCCCG GATCGAGATA GTATATGATG CATATTCTTT AAATATAGAT   50
EcoRI

AAAGTTATAG AAGCAATAGA AGATTTAGGA TTTACTGTAA TATAAATTAC  100
   -35        promoter      -10                      ┌────────
   ───           ──────     ───                      
ACTTTTAAAA AGTTTAAAAA CATGATACAA TAAGTTATGG TtGGAATTGT  150
                                                 ──────
   lac operator                        ribosome binding site
   ──────────────────────────┐           ┌──────────────────┐
TATCCGCTCA CAATTCCAAC TTATGATTAA AATTTTAAGGA GGTGTATTT   200
──────────────────────               └──────────┘ cat  ATG  ← START CODON lacZ'

NdeI
```

Fig. 2

ANAEROBE TARGETED ENZYME-MEDIATED PRODRUG THERAPY

This application is a continuation-in-part of U.S. Ser. No. 09/803,330, filed Mar. 9, 2001, now abandoned. This application is also a continuation-in-part of U.S. Ser. No. 10/151,069, filed May, 17, 2002, now U.S. Pat. No. 6,652,849; which is a continuation of U.S. Ser. No. 08/686,502 filed Jul. 23, 1996, now U.S. Pat. No. 6,416,754; which is a continuation of U.S. Ser. No. 08/465,932, filed Jun. 6, 1995, now abandoned; which is a continuation of U.S. Ser. No. 08/227,313, filed Apr. 13, 1994, now abandoned; which is a continuation of U.S. Ser. No. 08/206,430, filed Mar. 3, 1994, now abandoned. All of these applications are incorporated herein by reference.

FIELD OF THE INVENTION

This invention relates to genetically-engineered bacteria which, under anaerobic conditions present in a solid tumor and produce an enzyme capable of catalyzing the conversion of a prodrug to its cytotoxic product in situ and methods of treating tumors using the same.

References

Alexander et al., *Tetrahedron Lett.* 32:3269–3272, 1991.
Anlezark et al., *Biochem. Pharmacol.* 44:2289–2295, 1992.
Antonio et al., *Br. J. Cancer* 62:909–914, 1990.
Austin E A and Hubert B E, *Mol. Pharmacol.* 43:380–387, 1993.
Bagshawe, K D, *Br. J. Cancer* 60:275–281, 1989.
Bagshawe, K D, supra; Senter, P D, *FASEB J.* 4:188–193, 1990.
Beguin et al., *J. Bacteriol.* 162:102–105, 1985.
Boland et al., *Biochem. Pharmacol.* 41:867–875, 1991.
Bosslet et al., *Br. J. Cancer* 65:234–238, 1992.
Brehm et al., *Appl. Microbiol Biotechnol.* 36:358–363, 1991.
Brizel D M et al., Cancer Res. 56: 941–943, 1996.
Brown, J M, *Radiat. Res.* 64:633–647, 1975.
Brown, J M and Hirst D G, *Br. J. Cancer* 45:700–708, 1982.
Brown, J M and Lemmon M J, *Cancer Res.* 50:7745–7749, 1990.
Brown et al., *J. Natl. Cancer Inst.* 64:605–611, 1979.
Brown et al., Int. J. Rad. Oncol. Biol. Phys. 7:695–703, 1981.
Brown J M, Mol Med Today 6(4):157–62, 2000.
Carey et al., *Europ. J. Cancer* 3:37–46, 1967.
Chambers et al., *Gene* 68:139–149, 1988.
Cobb et al., *Biochem. Pharmacol.* 18:1519–1527, 1969.
Connors et al., *Biochem. Pharmacol.* 22:1971–1980, 1973.
Davis, J B, *Annals N.Y. Acad. Sci.* 121:404–407, 1964.
Davis T O et al., J Mol Microbiol Biotechnol, 2(1):59–69, 2000.
de Groot F M et al., *J. Med. Chem.*, 43, 3093–3102, 2000.
de Groot F M et al., *J. Med. Chem.*, 42, 5277–5283, 1999.
Engelbart, K, and Gericke D, *Cancer Res.* 24:239–243, 1964.
Fitzgerald et al., *Biochem. Soc. Trans.* 20:731–734, 1992.
Fox, M E, et al., Gene Therapy. 3:173–178, 1996.
Germane, S. and Zidermane A, *Eksp. Klin. Farmakoter* 16:36–44, 1987.
Gordon et al., *Carcinogen* 12:2393–2396, 1991.
Graves et al., *Proc. Natl. Acad. Sci. USA* 82:1653–1657, 1985.
Gray, L H et al., Br. J. Radiol. 26:638–648, 1953.
Haisma et al., *Br. J. Cancer* 66:474–478, 1992.
Hamstra D A et al., *Human Gene Therap.* 10:1993–2003, 1999.
Hirst et al. *Br. J. Cancer* 46:109–116, 1982.
Hockel M et al., Cancer Res. 56: 4509–4515, 1996.
Houba P H et al., *Biochem Pharmacol* 15; 57(6):673–80, 1999.
Houba P H et al., Br J Cancer 84(4):550–557, 2001.
Jain, R K, *J. Natl. Cancer Inst.* 81:570–576, 1989.
Jefferson et al., *Proc. Natl. Acad. Sci. USA* 83:8447–8451, 1986.
Jones, D T and Woods D R, Microbiol. Rev. 484–524, 1986.
Kaplan, J C and Beutler E, *Nature* 217:256–261, 1968.
Knox et al., *Biochem. Pharmacol.* 37:4661–4669, 1988.
Kulinkovich, L N and Timoshchuk V. A., Obshch. Khim. 53:1649–1651, 1983.
Laemmli, U. K (*Nature* 227:680–685, 1970.
Lawrence, T S, et al., Cancer Res. 58: 2588–2593, 1998.
Leenders, R G G et al., Bioorg. Med. Chem., 7:1597, 1999.
Lemmon, M L, et al., Gene Therapy. 4:791–796, 1997.
Maftouh et al. *Drug Metab. Dispos.* 12:111–119, 1984.
Malmgren and Flanagan, *Cancer Res.* 15:473, 1955.
Melton R G and Sherwood R F, *J Natl Cancer Inst* 88(3–4):153–65, 1996.
Meyer D L et al., *Cancer Res.*, 53(17):3956–63, 1993.
Minton N P and Morris J G, *J. Gen. Microbiol.* 127:325–331, 1981.
Minton, N P, et al., In: S. P. Borriello (ed.) CLINICAL AND MOLECULAR ASPECTS OF ANAEROBES, pp. 187–201: Wrightson Biomedical Publishing Ltd., 1990.
Minton et al., In: MOLECULAR BIOLOGY AND BIOTECHNOLOGY OF EXTREMOPHILES 281–320, Blackies Publishing, Herbert, R. A., J Sharp, eds. 1992.
Minton et al., *Vector Systems for the genetic analysis of Clostridium acetobutylicum*, 187–201, In: CLINICAL AND MOLECULAR ASPECTS OF ANAEROBES, Borriello, S. P., eds., Wrightson Biomedical Publishing, 1993.
Minton N P et al., *FEMS Microbiol Rev* 17(3):357–64, 1995.
Mose et al., *Cancer Res.* 24:212–216, 1964.
Möse, J R and Möse G, Z. *Krebsforsch* 63:63–74, 1959.
Mose, J R and Mose G, Cancer Res. 24:212–216, 1964.
Mullen et al., *Proc. Natl. Acad. Sci. USA* 89:33–37, 1992.
Narberhaus F and Bahl H J, Bacteriol. 3282–3289, 1992.
Niculescu-Duvaz I et al., Anticancer Drug Des 14(6): 517–38, 1999.
Noe et al., *Brit. J. Haem.* 80:285–292, 1992.
Oberley et al., *Amer. J. Pathol.* 137:199–214, 1990.
Oultram, J D et al., *FEMS Microbiol. Letts.* 56: 83–88, 1988.
Petitdemange et al., *Biochem. Biophys. ACTA* 421:334–347, 1976.

Roberts et al., *Biochem. Biophys. Res. Commun.* 140:1073–1078, 1986.

Rockwell et al., *J. Natl. Cancer* 49:735–749, 1972.

Rosenberg, S A, *JAMA* 268:2416–2419, 1992.

Schlechte H and Albe B, *Zbl. Bakt. Hyg. A* 268:347–356, 1988.

Senter P D et al., Cancer Res. 49: 5789–5792, 1989.

Shuttleworth et al., *Gene* 58:283–295, 1987.

Stahl et al., 246–256, 1984.

Stone et al., *Int. J. Radiat. Oncol. Biol. Phys.* 20:987–995, 1991.

Swinfield et al., *Gene* 87:79–89, 1990.

Thiel et al., ONCOLYSIS BY CLOSTRIDIA. IV. EFFECTS OF CLOSTRIDIA AND CHEMOTHERAPEUTIC AGENTS ON RODENT TUMORS, 242, 1964.

Towbin et al., *Proc. Natl. Acad. Sci. USA* 76:4350–4354, 1979.

Twentyman et al., *J. Natl. Cancer Inst.* 64:595–604, 1980.

Vitols K S et al., Pteridines 1:65–70, 1989.

Vitols K S et al., Cancer Res. 55:478–481, 1995.

Walter K A et al., J. Bacteriol. 7149–7158, 1992.

Wang et al., *Cancer Res.* 52:4484–4491, 1992.

Weenen et al., *Eur. J. Cancer Clin. Oncol.* 20:1984, 1984.

Wilson et al., *Cancer Res.* 62:1425, 2002.

Workman et al., *Cancer Chemother. Pharmacol.* 16:9–14, 1986.

Ysern et al., *J. Biol. Chem.* 264:7765–7767, 1989.

BACKGROUND OF THE INVENTION

Despite the success of modern chemotherapy in the treatment of certain types of leukemia and lymphoma and some other relatively rare cancers, few current anticancer therapies have met with significant clinical success in treatment of the most common forms of cancer. The poorly responsive cancers are typically solid tumors comprising both proliferating and non-proliferating cells. Typically, the anticancer drugs used today are effective predominantly against rapidly proliferating tumor cells, and are toxic to rapidly proliferating non-cancerous cells. Two general approaches are currently being pursued to overcome this problem. First, there is an intensive search for new drugs that are selective for cancer cells. A second strategy is that of targeting new or existing drugs specifically to tumors. Many attempts at applying this strategy have relied on monoclonal antibodies (Mabs) to carry a drug or toxin to the tumor. A major problem with this approach is tumor cell heterogeneity and the inability to deliver antibody conjugates to every tumor cell (Jain, 1989). One way of overcoming this problem is the use of enzyme-antibody conjugates which activate prodrugs to form diffusible cytotoxins (Bagshawe, 1989). This approach has been called antibody-directed enzyme prodrug therapy (ADEPT). The two-step ADEPT process requires the conjugation of a suitable enzyme to a monoclonal antibody which localizes the enzyme to the tumor. When most of the nonbound antibody-enzyme conjugate has been cleared, a prodrug is administered which can be activated by the enzyme to a cytotoxic species (Bagshawe, 1990). Though the ADEPT strategy is promising, it has a number of problems. First, the large majority of the Mab-enzyme conjugates do not localize in the tumor, and studies have shown that concentrations of the active drug in normal tissues can be greater than in the tumor (Antonio et al., 1990). Also, MAbs of high enough specificity are not available for many tumors. See, also Melton et al., 1996.

Other targeting approaches include the use of recombinant toxins, such as growth factors fused to a bacterial toxin (Fitzgerald et al., 1992), and the use of tumor-infiltrating lymphocytes genetically engineered to produce a protein such as tumor necrosis factor (TNF) (Rosenberg, 1992). No reports of improved activity of any of these targeting strategies has yet appeared.

In still another approach, a gene for the cancerostatic polypeptide Colicin E3 was introduced into an uncharacterized mixture of endogenous plasmids in *C. oncolyticum* (*C. butyricum* M-55, renamed because of its oncolytic activity; Schlechte, et al., 1988). This approach, however, was unsuccessful based on the inability to transform *C. oncolyticum* and the corresponding inability to show that the recombinants were expressing active protein. In addition, this approach is based on an anticancer agent that is a protein rather than a low molecular weight compound. At the present time, low molecular weight compounds constitute the majority of chemotherapeutic agents.

Human solid tumors, which make up more than 90% of all human cancers are known to comprise a hypoxic environment in that they are considerably less well oxygenated than normal tissues. Recent cancer treatment strategies focused on this aspect include the use of drugs that are toxic only under hypoxic conditions, e.g., tirapazamine, and gene therapy approaches based on the use of transcription factors that are inducible under hypoxic conditions, e.g., hypoxia-inducible factor 1 (HIF-1). See, e.g., Brown, 2000.

Despite advances in cancer treatment, significant side effects due to the toxicity of the chemotherapeutic agents in current use remains a problem. Gene therapy strategies have been attempted and are the subject of ongoing clinical trials. However, the lack of specificity of delivery systems and toxic side effects due to those delivery systems must be overcome in order for such strategies to have clinical relevance.

Accordingly, a need exists for selective targeting of toxic chemotherapeutic agents to solid tumor tissue without exposing healthy tissue to the agent.

SUMMARY OF THE INVENTION

The present invention relates to transformation of obligately anaerobic bacteria with an recombinant expression vector comprising a coding sequence for an enzyme capable of catalyzing the conversion of a prodrug into a cytotoxic agent in vivo.

In one embodiment, the anaerobic bacteria is a species of the genus *Clostridium*, and the transformed bacteria is capable of high level replication in tumor tissue in vivo. When injected into a subject, the genetically engineered *Clostridium* proliferate and produce the encoded enzyme in the hypoxic/necrotic regions of tumor tissue with little or no expression in non-cancerous tissue. The tumor-bearing individual is treated systemically with a prodrug which is converted to its toxic counterpart by the enzyme which, due to the anaerobic nature of the bacteria producing it, is specifically expressed in the hypoxic/necrotic regions of the tumor.

The invention also relates to recombinant bacteria comprising the coding sequence for an enzyme capable of converting a prodrug to a chemotherapeutic agent. The bacteria are transformed under conditions effective to achieve a high level of proliferation in an in vivo tumor. These conditions include one or more of the following: (i) presence of an inhibitor of nuclease activity; (ii) a temperature of less than about 10° C. and above 0° C.; or (iii) an environment having an oxygen level that maintains growth of said anaerobe. In a preferred embodiment, all three conditions are maintained during contact of the anaerobe with the recombinant expression vector. In other preferred embodiments, the temperature is less than about 5° C. but above freezing (i.e., above the freezing temperature of the medium in which the anaerobe and the vector are held, typically about 0° C.).

In a preferred embodiment, *Clostridium sporogenes* is the anaerobe.

Enzymes capable of catalyzing the conversion of a prodrug into a chemotherapeutic agent for expression in *Clostridium* spp. include cytosine deaminase, nitroreductase, β-glucuronidase, β-galactosidase, carboxypeptidase, alkaline phosphatase and β-lactamase.

Glucuronide conjugates of epirubicin, doxorubicin, 5-fluorocytosine, CB1954, 4-hydroxycyclophosphamide or hydroxyanaline mustard, etoposide phosphate, doxorubicin phosphate, mitomycin C phosphate and 5-fluorocytosine are exemplary prodrugs.

The invention also provides a method of targeting a chemotherapeutic agent to a tumor in a tumor-bearing individual by administering to the individual an amount of recombinant *Clostridium* bacteria capable of proliferating and producing an enzyme effective to catalyze the conversion of a prodrug into a chemotherapeutic agent in the hypoxic/necrotic environment of the tumor; and systemically administering a prodrug that is converted at the site of the tumor to a toxic chemotherapeutic agent by the enzyme produced by the bacteria.

These and other objects and features of the invention will become more fully apparent when the following detailed description of the invention is read in conjunction with the accompanying drawings.

BRIEF DESCRIPTION OF FIGURES

FIG. 1 illustrates the construction of a clostridial vector (pNTR500F) expressing nitroreductase (NTR).

FIG. 2 illustrates the nucleotide sequence (SEQ ID NO:1) of the modified *Clostridium pasteurianum* Fd gene promoter. One of the MboI sites employed in the original cloning of the 64 bp fragment has been bracketed. The nucleotides shown 5' to this MboI site, including the EcoRI site, are derived from M13mp7. The −35 and −10 promoter motifs are overlined, and the ribosome binding site and inserted lac operator motif are boxed. Nucleotides created by site directed mutagenesis are shown in lower case. The boxed ATG corresponds to that of the original ferrodoxin structural gene, but becomes that of the lacZ' gene in all plasmids described in FIGS. 3–4.

DETAILED DESCRIPTION OF THE INVENTION

I. Definitions

Figure 3:
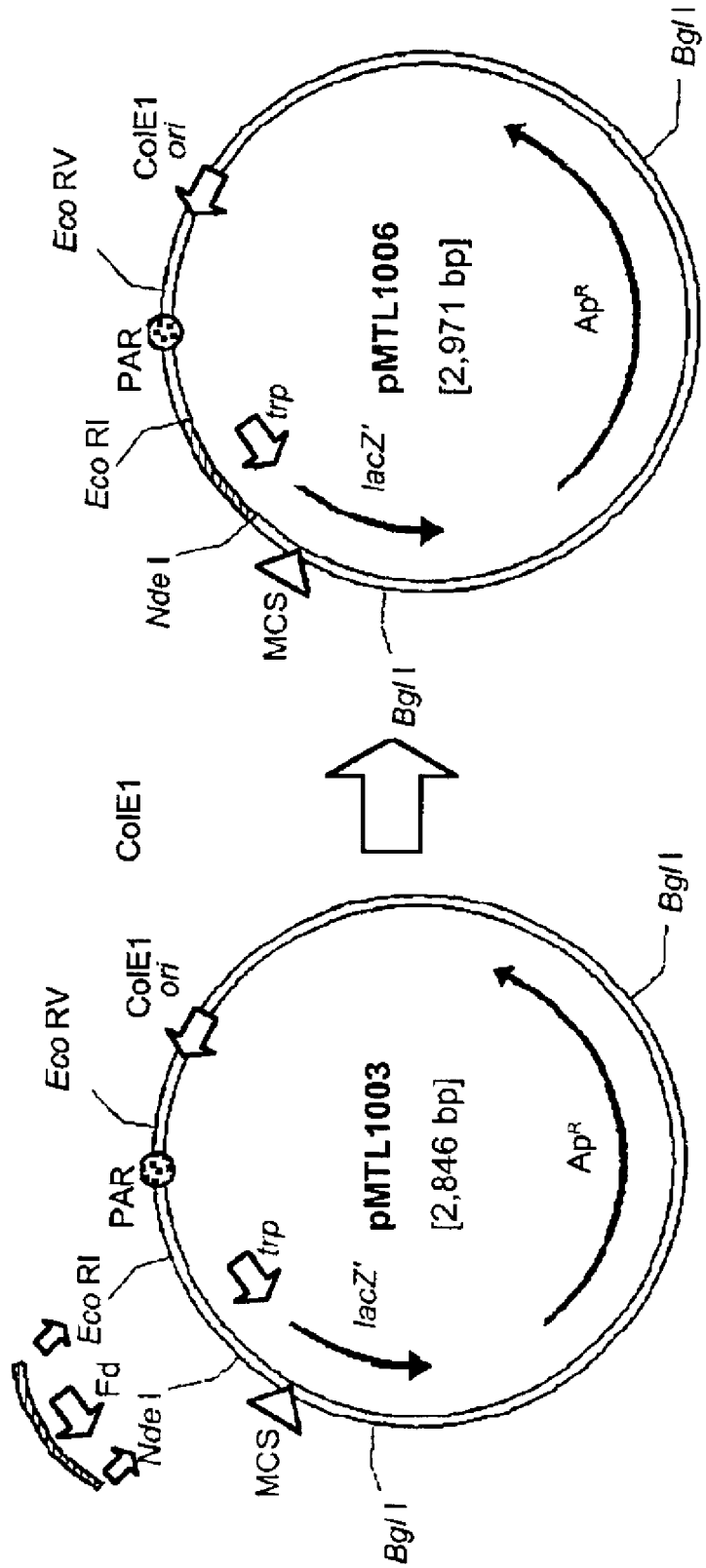
FIG. 3 illustrates the construction of pMTL1006 plasmid, which is derived from pMTL1003 by replacing the trp promoter of the latter with the modified ferrodoxin (Fd) promoter. The MCS is that of pMTL20 (Chambers et al.). Key: MCS=multiple cloning site; Ap=ampicillin; $^R$=resistance; PAR=the partition locus of plasmid pSC101; trp=the *E. coli* trpE promoter; ori=origin of replication; and Fd=ferrodoxin gene promoter.

Unless otherwise indicated, all technical and scientific terms used herein have the same meaning as they would to one skilled in the art of the present invention. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

All publications cited herein are expressly incorporated herein by reference for the purpose of describing and disclosing compositions and methodologies which might be used in connection with the invention.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native cell.

The terms "vector", as used herein, refer to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art. A cloning or expression vector may comprise additional elements, e.g., the expression vector may have two replication systems, thus allowing it to be maintained in two organisms, e.g. in human cells for expression and in a prokaryotic host for cloning and amplification. Cloning and expression vectors will typically contain a selectable marker.

As used herein, the term "promoter" refers to a nucleic acid sequence that functions to direct transcription of a downstream gene. The promoter will generally be appropriate to the host cell in which the target gene is being expressed. The promoter together with other transcriptional and translational regulatory nucleic acid sequences (also termed "control sequences") are necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. A promoter may be constitutive or inducible and may be a naturally occurring, engineered or hybrid promoter.

The term "control sequences" refers to DNA sequences necessary for the expression of an operably linked coding sequence in a particular host organism. The control sequences that are suitable for prokaryotes, e.g., include a promoter, optionally an operator sequence, and a ribosome binding site. Eukaryotic cells are known to utilize promoters, polyadenylation signals, and enhancers.

As used herein, the term "operably linked" relative to a recombinant DNA construct or vector means nucleotide components of the recombinant DNA construct or vector that are directly linked to one another for operative control of a selected coding sequence. Generally, "operably linked" DNA sequences are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons).

Exemplary computer programs which can be used to determine identity between two sequences include, but are not limited to, the suite of BLAST programs, e.g., BLASTN, BLASTX, and TBLASTX, BLASTP and TBLASTN, publicly available on the Internet. See, also, Altschul, S. F. et al., 1990 and Altschul, S. F. et al., 1997.

Sequence searches are typically carried out using the BLASTN program when evaluating a given nucleic acid sequence relative to nucleic acid sequences in the GenBank DNA Sequences and other public databases. The BLASTX program is preferred for searching nucleic acid sequences which have been translated in all reading frames against amino acid sequences in the GenBank Protein Sequences and other public databases. Both BLASTN and BLASTX are run using default parameters of an open gap penalty of 11.0, and an extended gap penalty of 1.0, and utilize the BLOSUM-62 matrix. [See, Altschul, et al., 1997.]

A preferred alignment of selected sequences in order to determine "% identity" between two or more sequences, is performed using e.g., the CLUSTAL-W program in MacVector version 6.5, operated with default parameters, including an open gap penalty of 10.0, an extended gap penalty of 0.1, and a BLOSUM 30 similarity matrix.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. E.g., "maximum stringency" typically occurs at about Tm-5° C. (5° below the Tm of the probe); "high stringency" at about 5–10° below the Tm; "intermediate stringency" at about 10–20° below the Tm of the probe; and "low stringency" at about 20–25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, e.g., Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C.

As used herein, "recombinant" includes reference to a cell or vector, that has been modified by the introduction of a heterologous nucleic acid sequence or that the cell is derived from a cell so modified. Thus, recombinant cells express genes that are not found in identical form within the native (non-recombinant) form of the cell or express native genes that are otherwise abnormally expressed, under expressed or not expressed at all as a result of deliberate human intervention.

As used herein, the terms "transformed", "stably transformed" or "transgenic" with reference to a mammalian cell means the mammalian cell has a non-native (heterologous) nucleic acid sequence integrated into its genome which is maintained through two or more generations.

As used herein, the term "expression" refers to the process by which a polypeptide is produced based on the nucleic acid sequence of a gene. The process typically includes transcription and translation, however, in some cases the term "expression" may be used to refer to transcription in the absence of translation.

As used herein, the terms "high level proliferation" and "high level replication" refers to bacterial replication at a level that typically results in greater than $10^6$ and more typically greater than $10^7$ bacteria per gram of tumor in a solid tumor in vivo in an animal. In a preferred embodiment, the term is with reference to growth of anaerobic bacteria of the genus Clostridium in solid tumors.

The term "under conditions effective to achieve" refers to the laboratory conditions of temperature, atmospheric oxygen level, and/or presence or absence of a nuclease inhibitor that are required to transform an obligate anaerobic bacteria species to yield a transformed bacteria capable of such high level proliferation.

II. Compositions and Methods of the Invention.

A. Selective Infection of Tumor Cells

The ability of spores of the genus Clostridium to germinate in hypoxic/necrotic tissue is widely known. Tetanus and gas gangrene, for example, result from successful colonization of necrotic tissue by pathogenic strains of these organisms. In the absence of necrotic tissue, however, these organisms are inert. In 1955, Malmgren and Flanagan, showed that tumor-bearing mice died of tetanus within 48 hours of intravenous injection of C. tetani spores, whereas non tumor-bearing animals were unaffected. Microscopic observations confirmed that vegetative forms were localized solely in the tumor tissue. Mose et al., 1959 and 1964, later reported that a nonpathogenic clostridial strain, C. butyricum M-55, localized and germinated in solid Ehrlich tumors, causing extensive lysis without concomitant effect on normal tissues. These observations have been confirmed and extended by a number of investigators using tumors in mice, rats, hamsters, rabbits, and man (Carey et al., 1967; Engelbart et al., 1964; Thiel et al. 1964).

It was a common finding, particularly with the very large tumors used in the experiments performed in the early 1960's, that the extensive lysis of a tumor often produced death of the animal, presumably due to toxins released into the blood stream from the clostridia or the lysed cells. The present invention does not require cellular lysis for activity. In fact, it is advantageous to stop the reaction before extensive cellular lysis has occurred.

Intravenously injected clostridial spores have been demonstrated to exhibit specificity for tumors by localization to, and germination in, the hypoxic/necrotic tissue of tumors. The feasibility of clostridial-directed enzyme prodrug therapy (CDEPT) was demonstrated by cloning the Escherichia coli B gene encoding nitroreductase (which converts the prodrug CB1954 to a highly toxic bifunctional alkylating agent) into a clostridial expression vector and introducing the resultant plasmid into Clostridium beijerinckii (formerly C. acetobutylicum) NCIMB 8052 (Minton et al., 1995).

B. Genetically-Engineered Anaerobic Microorganisms

1. Nitroreductase Expressing C. acetobutylicum (a.k.a. C. beijerinkii)

Nonpathogenic strains of clostridia which allow genetic manipulations include, but are not limited to anaerobic bacteria, particularly members of the genus Clostridium. In exemplary embodiments of the present invention, the bacteria is C. acetobutylicum (later renamed C. beijerinkii) or C. sporogenes (of which C. oncolyticum, previously known as C. butyricum, is a member).

In studies in support of the invention, C. acetobutylicum (later renamed C. beijerinkii) was used, as will be described below. C. acetobutylicum has a long history, dating back to World War I for use in producing acetone and butanol, and more recently has been manipulated molecularly to exploit its biotechnological potential (Minton et al., 1993). C. acetobutylicum germinates in tumor tissue, and tumor lysis has been reported for this strain (Mose et al., 1964). Antitumor activity is optimally produced by spores rather than the vegetative form (Mose and Mose, supra), and C. acetobutylicum produces spores under the conditions present in the targeted tumor. The nonpathogenic clostridial strain, C. acetobutylicum (C. beijerinkii strain NCIB 8052), is exemplified herein to demonstrate the basis for the present invention.

As described in Example 1, Clostridium beijerinkii, was genetically engineered to produce the E. coli-derived nitroreductase gene in experimental tumors in mice, (see also, Lemmon et al., 1997). A recombinant plasmid capable of directing the expression of the E. coli nitroreductase (ntr) gene in C. acetobutylicum (later renamed C. beijerinkii) was constructed, as described in detail in Example 1 and shown in FIGS. 1–4. In essence, a Nde1 site was created 'over' the translational start codon of the ntr gene allowing its subsequent insertion into pMTL500F immediately adjacent to the clostridial ferrodoxin (Fd) promoter and ribozyme binding site (RBS).

Following construction, the vector pNTR500F was transformed into B. substilis and C. acetobutylicum for testing in vitro and in vivo. In vitro expression of the recombinant E. coli NTR in bacterial cultures was quantified using a spectrophotometric enzyme activity assay that measured NTR activity in supernatant and cell pellet fractions of transformed clostridial cultures. This assay, based upon the reduction of dichlorophenol-indophenol in the presence of NADH, demonstrated that clostridia transformed with the plasmid containing the E. coli ntr gene (pNTR500F) exhibited a 200-fold increase in NTR activity when compared to the endogenous activity of the parental wild-type strain in mid-log phase cultures.

Figure 5A:
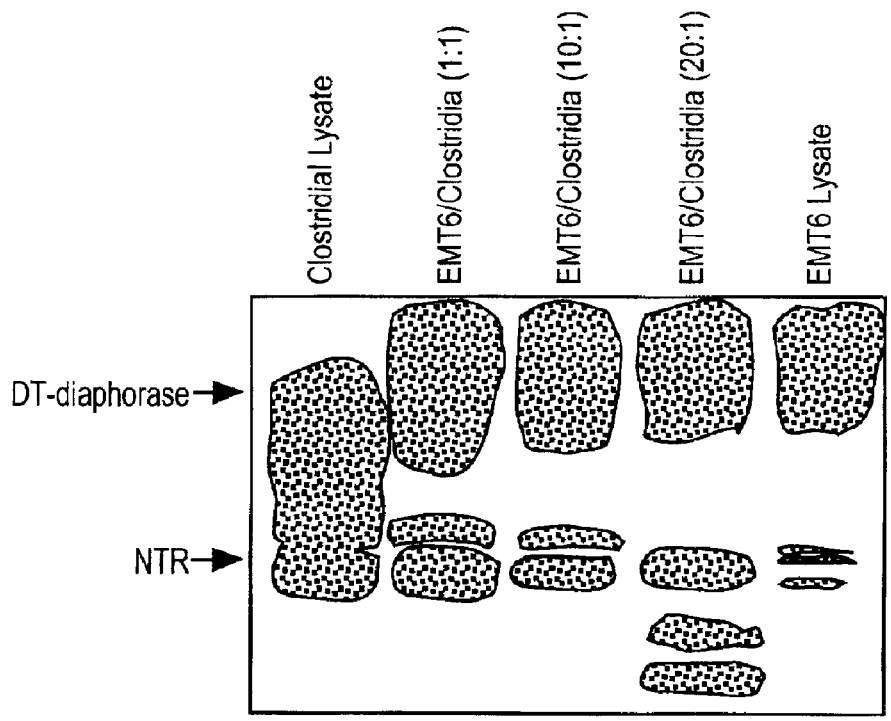
FIG. 5A is an artists rendering of a polyacrylamide gel showing detection of recombinant nitroreductase activity and protein in tumor homogenates. Tested on the nondenaturing polyacrylamide gel were mixtures of EMT6 tumor lysate and *C. acetobutylicum* expressing nitroreductase; EMT6 tumor lysate alone; and lysate of NTR-expressing *C. acetobutylicum* alone.
Figure 5B:
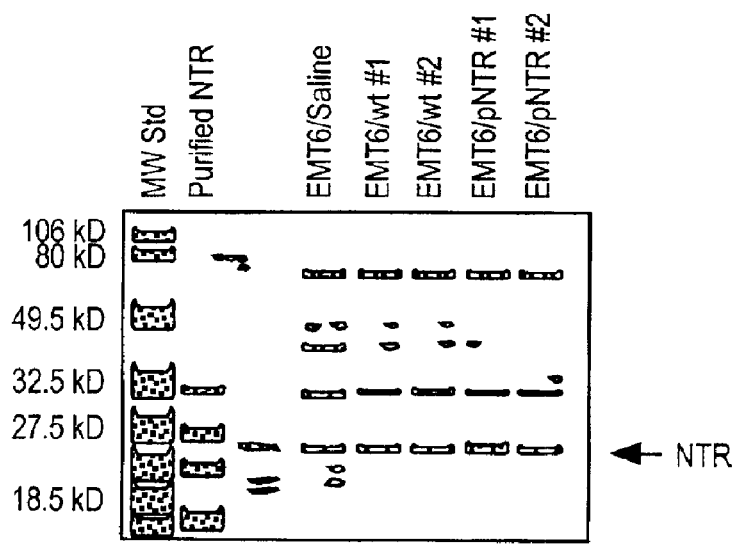
FIG. 5B is an artists rendering of a Western blot, stained with antibody raised against *E. coli* NTR. The lanes contained molecular weight markers; purified nitroreductase as standard; EMT6 tumor lysates derived from tumor-bearing mice treated with saline; $10^8$ spores from wild type (wt) or NTR-expressing *C. acetobutylicum*.

In other in vitro tests, E. coli NTR activity was visualized in nondenaturing polyacrylamide gels and by Western blot, and the results are shown in FIGS. 5A and 5B. The results demonstrated that *C. acetobutylicum* spores were able to facilitate the expression of recombinant NTR in vivo and that recombinant NTR could be detected in tumor homogenates.

Figure 6:
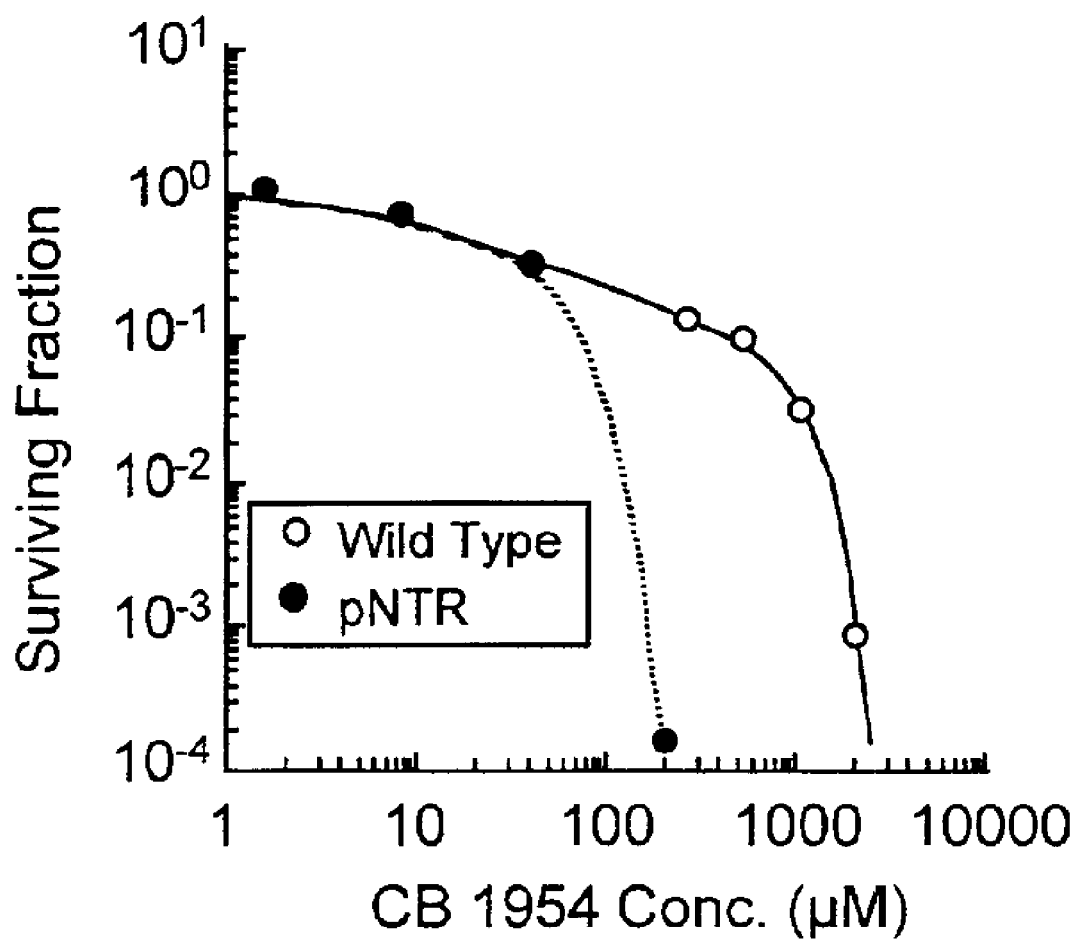
FIG. 6 illustrates the cell killing of SCCVII cells in vitro exposed to CB1954, NADH, and supernatants from wild type (wt) or recombinant *C. acetobutylicum*.

The ability of recombinant *C. acetobutylicum* to activate CB1954 was also tested in vitro, also as described in Example 1. Briefly, recombinant and wild type *C. acetobutylicum* were inoculated into medium, and after overnight incubation, the cultures were centrifuged and the supernatant collected. The supernatant was added to cultures of SCCVII tumor cells, along with addition of various concentrations of CB1954 in DMSO. After incubation for two hours, the cells were counted by hemocytometer, and appropriate dilutions plated and incubated for colony growth. The results are shown in FIG. 6, and show that the supernatant from the transformed *C. acetobutylicum* was capable of enhancing the toxicity of CB1954 by approximately 10-fold.

In vivo studies with three different transplanted mouse tumors, EMT6, SCCVII and RIF1 tumors and with human colon carcinoma HT29 transplanted into immune-deficient SCID mice were performed, also as described in Example 1. Tumors were injected with spores of control and recombinant *C. acetobutylicum* when the subcutaneous tumors reach a diameter of between approximately 0.5 and 1 cm. The prodrug CB1954 was injected into the tumor-bearing mice at different times during the growth of the *C. acetobutylicum* and the response of the tumor was measured by counting the total clonogenic cells per tumor 24 hrs after treatment and by regrowth delay. Upon analysis, it was observed that the level of viable *clostridia* in the tumors were approximately $10^5$ to $10^6$ bacteria per gram of tumor.

Together, the in vitro and in vivo studies established that an active foreign enzyme can be selectively expressed in tumors without detectable expression of the exogenous enzyme in normal tissues. This is accomplished following intravenous injection of the inactive spore form of the bacteria, exemplified by recombinant *C. beijerinckii*, which upon transition to a reproductive state, expressed the *E. coli* nitroreductase gene.

2. Cytosine Deaminase-expressing *C. sporogenes*

In other studies performed in support of the invention, *C. sporogenes* was transformed with a gene for expression of cytosine deaminase. Prior to the present invention, attempts to transform *C. sporogenes* (of which *C. oncolyticum* is a member) were unsuccessful and the literature lacked information as to how to transform strains of *C. sporogenes*. As will be described, an expression vector was constructed and an electroporation technique was developed that resulted in successful transformation of *C. sporogenes*. Further, in studies where transformed spores were injected into mice, it was demonstrated that *C. oncolyticum* and its closely related strain *C. sporogenes* gave $10^8$ to $2 \times 10^8$ bacteria/g of tumor, a level of bacterial replication that is practical for clinical application of the present invention.

A. Vector Construction and Transformation

Figure 7:
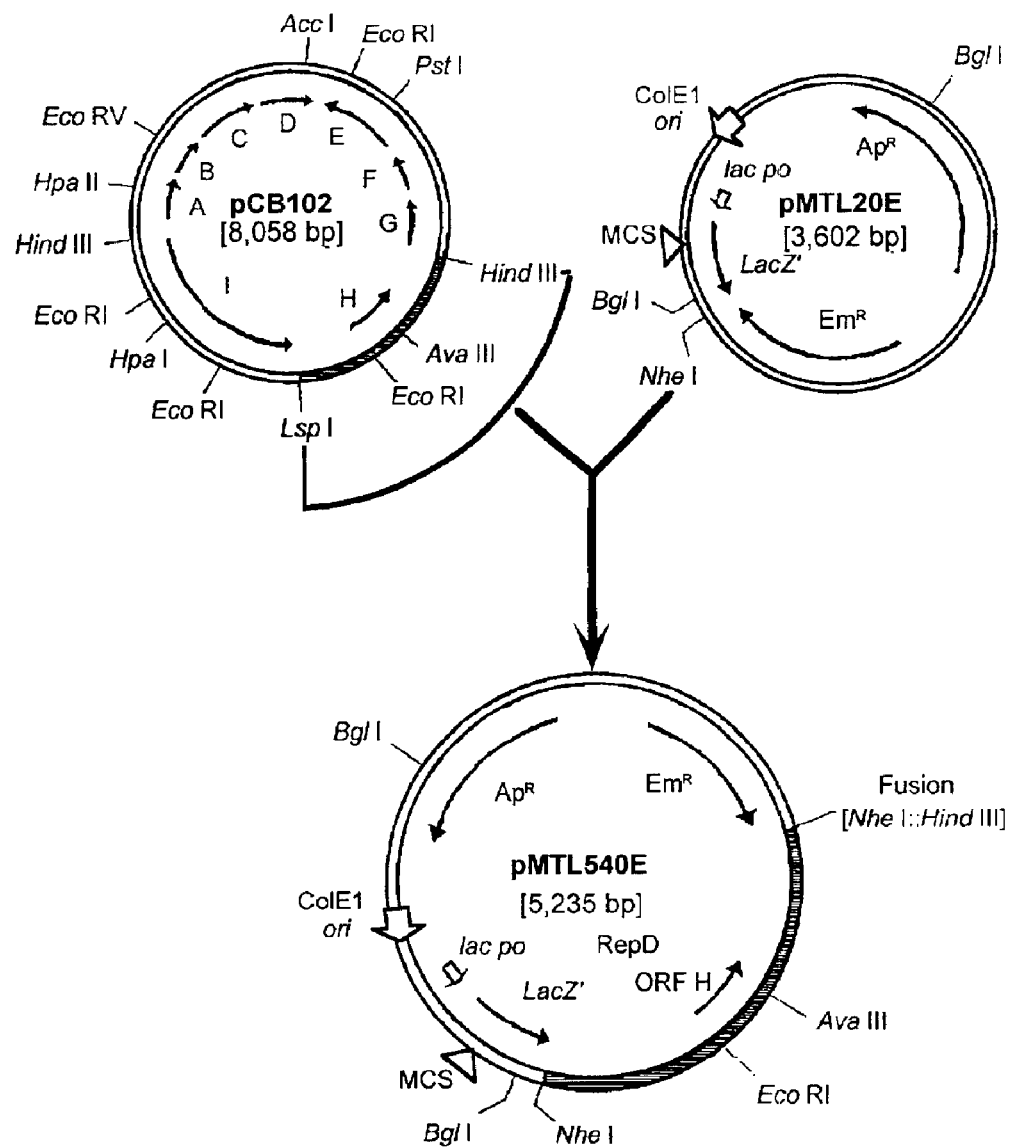
FIG. 7 illustrates construction of the cloning vector pMTL540E. Plasmid pCB102 was digested with HindIII and LspI, the fragments generated blunt-ended by treatment with T4 DNA polymerase and a 1.53 Kb fragment carrying the pCB102 minimal replicon regions isolated. The replicon probe vector pMTL20E was digested with NheI, blunt-ended T4 DNA polymerase, and ligated to the isolated LspI-HindIII fragment. The resultant plasmid was designated pMTL540E. The arrows within the map of pCB102 correspond to the major open reading frames (ORFs) identified following translation of its nucleotide sequence, where ORF H is though to play a role in replication.

Construction of the expression vector is described in Example 2A. Briefly, as illustrated in FIG. 7 plasmid pCB102 was digested with HindIII and LspI. The fragments generated were blunt-ended by treatment with T4 DNA polymerase and a 1.53 Kb fragment carrying the pCB102 minimal replicon regions was isolated. The replicon probe vector pMTL20E was digested with NheI, blunt-ended T4 DNA polymerase, and ligated to the isolated LspI-HindIII fragment. The resultant plasmid, shown in FIG. 7, was designated pMTL540E. The arrows within the map of pCB102 correspond to the major open reading frames (ORFs) identified following translation of its nucleotide sequence, where ORF H is though to play a role in replication.

Figure 8:
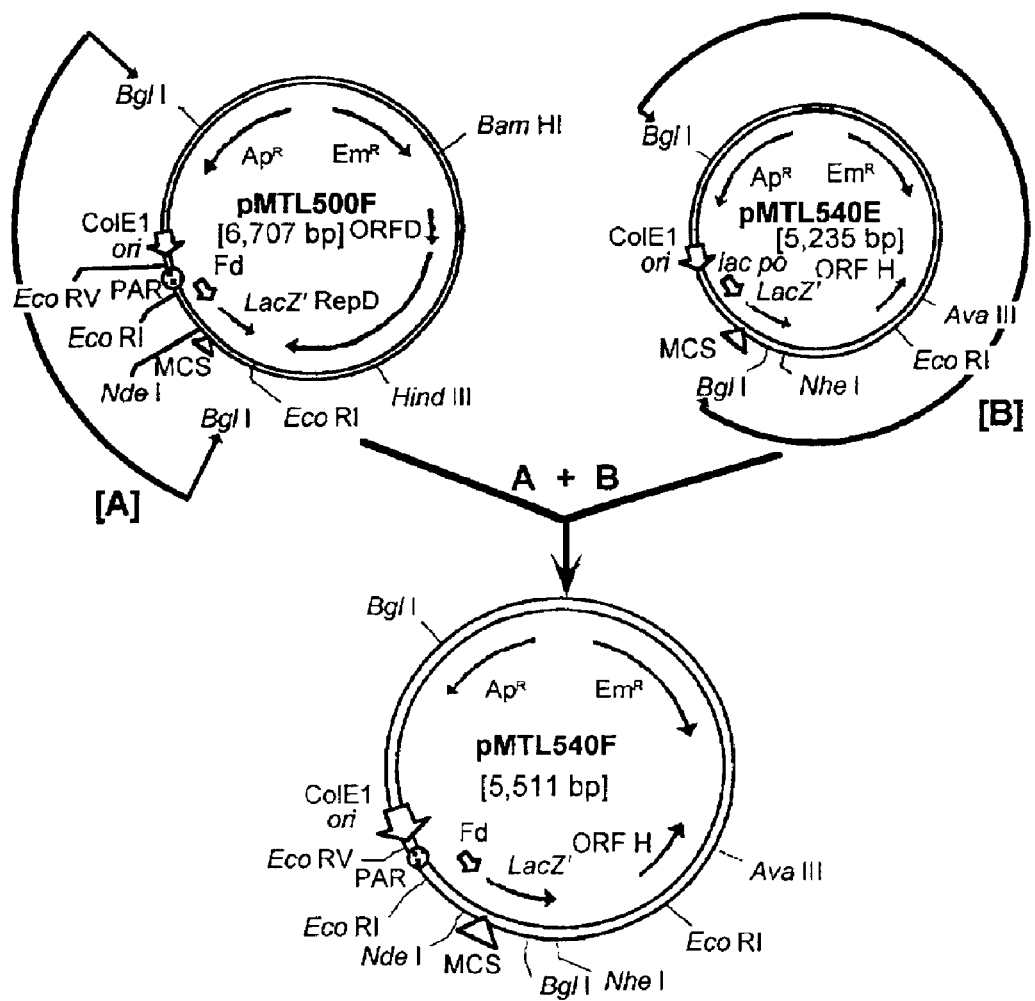
FIG. 8 illustrates the construction of the expression vector pMTL540F. Following cleavage of pMTL500E and pMTL540E with BgII, the indicated fragments (A and B) were isolated from the respective plasmids and ligated together to give plasmid pMTL540F.
Figure 9:
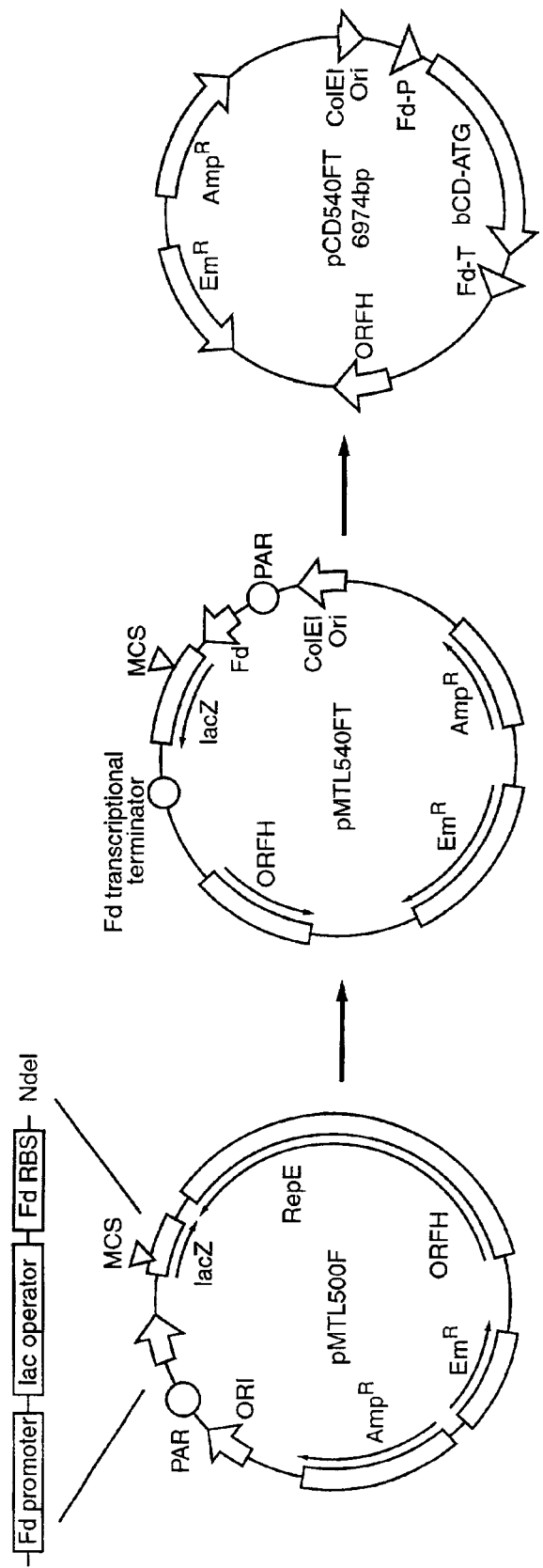
FIG. 9 illustrates construction of the expression vector pCD540FT which contains a coding sequence for expression of cytosine deaminase.

Next, as shown in FIG. 8, plasmids pMTL500E and pMTL540E were cleaved with Bg1I. The indicated fragments (A and B) were isolated from the respective plasmids and ligated together to give plasmid pMTL540F. The *E. coli* cytosine deaminase gene was inserted into the pMTL540F plasmid as described in Example 2A. The cytosine deaminase containing plasmid is shown in FIG. 9 and is referred to herein as pCD540FT and is abbreviated in some figures as "pCD".

*C. sporogenes* bacterial cells were transformed with the DNA plasmid vector pCD540FT by the electroporation procedure described in Example 2B. As noted above, until the present invention *Clostridia* ssp. have been difficult to transform to obtain expression of enzymes at a level sufficient to activate an anti-tumor prodrug. Technical obstacles relating to the extracellular secretion of endonucleases by the *clostridia* and relating to maintaining a "cold", oxygen-free or nearly oxygen free environment during transformation contribute to the difficulty of successful transformation. Successful transformation as used herein refers to transformation of the anaerobe to obtain expression of an enzyme capable of activating an anti-tumor prodrug at a clinically useful level, e.g., a "high level proliferation" of the transformed bacteria.

The transformation procedure described herein overcomes these technical obstacles to achieve a high level of proliferation in a tumor. As detailed in Example 2B, *C. sporogenes* was transformed under conditions effective to achieve a high level proliferation. These conditions included at least one of (i) the presence of an inhibitor of nuclease activity; (ii) a temperature of less than about 10° C. but above freezing of the medium containing the bacterial cells and the transformation vector, which is typically above about 0° C.; and (iii) an environment having an oxygen level that allows for or maintains growth of the anaerobic bacteria.

With respect to condition (i), the inhibitor of nuclease activity can be an inhibitor of endonucleases. That is, the inhibitor is capable of preventing the endonuclease activity of hydrolysis of interior bonds of ribonucleotide or deoxyribonucleotide chains. An exemplary inhibitor is aurintricarboxylic acid. Those of skill in the art are readily able to determine the amount of inhibitor required for effective inhibition.

With respect to condition (ii), the temperature for the transformation is maintained at less than about 10° C. but above freezing of the transformation medium, such as an electroporation buffer in which the bacterial cells and the recombinant vector are contacted. More preferably, the temperature is maintained at less than about 5° C., but above freezing. It will be appreciated that the freezing temperature will vary according to the components of the medium, but is typically about 0° C. In a more preferred embodiment, the temperature is less than about 4° C. but above freezing of the transformation medium.

With respect to condition (iii), the environment in which the transformation is conducted is controlled such that the oxygen level permits growth of the anaerobe. Such a "low-level" oxygen environment can be maintained by use of a hypoxic chamber or other suitable controlled environment. An exemplary "low level" oxygen environment is one having less than about 100 ppm oxygen, more preferably less than about 50 ppm oxygen, and most preferably less than about 10 ppm oxygen.

In the procedure described in Example 2B, *C. sporogenes* was successfully transformed under conditions that included (i), (ii) and (iii). More specifically, the DNAase inhibitor aurintricarboxylic acid was included in the transformation medium, an electroporation buffer; the temperature of the medium was maintained at less than about 4° C. and the surrounding atmosphere was controlled to be nearly oxygen free. The cold temperature and the low level oxygen were provided by the dry ice container described in Example 2B.

The transformation procedure involves contacting the anaerobic bacteria cells to be transformed with the recombinant expression vector. The cells and the vector can, for example, be brought into contact in a suitable transformation medium, such as an electroporation buffer. In one embodiment, contact of the cells and the vector is combined with electroporation to facilitate introduction of the vector into the cell.

B. In vitro Expression and Activity of Cytosine Deaminase

Figure 10:
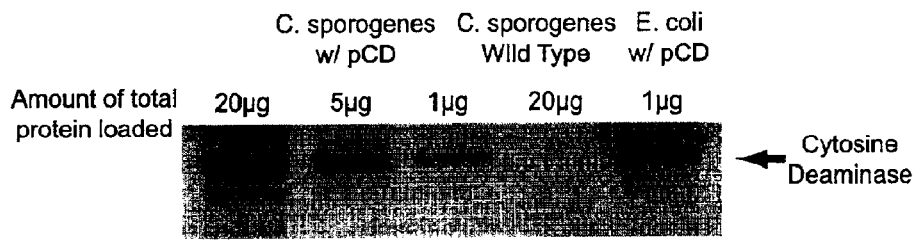
FIG. 10 shows a Western blot analysis of cytosine deaminase protein expression in transformed *C. sporogenes* (*C. sporogenes* w/pCD), wild type *C. sporogenes* (*C. sporogenes* wild type) and an *E. coli* control transformed with the same vector (*E. coli* w/pCD).

FIG. 10 shows Western blot analysis of cytosine deaminase protein expression in cell lysates of transformed *C. sporogenes* ("*C. sporogenes* w/pCD"), wild-type *C. sporogenes*, and *E. coli* transformed with the same vector ("*E. coli* w/pCD"). The blot clearly shows expression of cytosine deaminase by the transformed bacteria and an absence of cytosine deaminase in the wild type bacteria.

Figure 11:
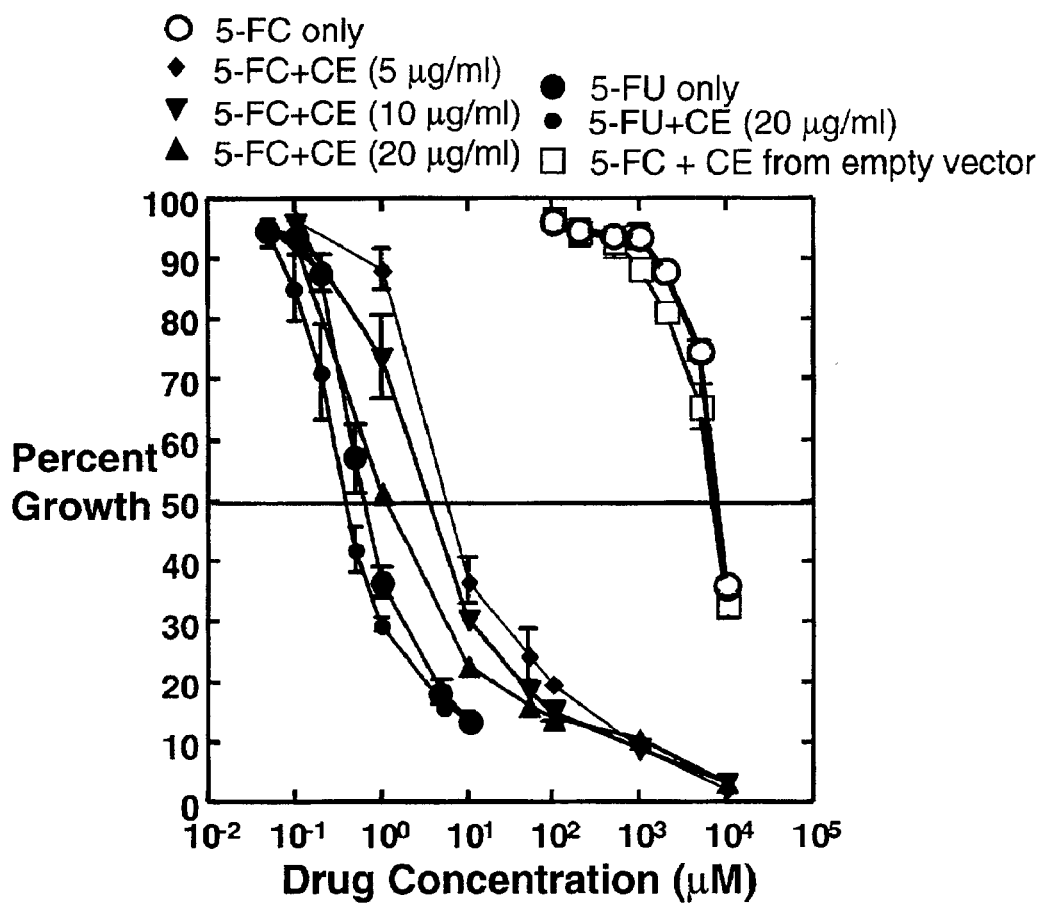
FIG. 11 shows the percent growth of SCCVII cells as a function of drug concentration when incubated with 5-fluorouracil (open circles, 5-FC only), 5-fluorouracil (larger closed circules; 5-FU only), 5-FC plus 5, 10 or 20 µg/ml of a cell extract ("CE") from recombinant *C. sporogenes* (diamonds, inverted triangles and triangles, respectively), or 5-FU plus 20 µg/ml of a cell extract from recombinant *C. sporogenes* (smaller closed circles), or 5-FU plus 20 µg/ml of a cell extract from an empty vector (open squares).

The function of the *C. sporogenes*-derived cytosine deaminase was tested by assaying its ability to convert the nontoxic 5-fluorocytosine (5-FC) to the toxic 5-fluorouracil (5-FU). FIG. 11 shows data for growth inhibition of SCCVII cells incubated with 5-FC alone (open circles), 5-FU alone (larger closed circles), or in the presence of various concentrations of cell extract ("CE" in the figure legend; "CE" concentrations of 5, 10, 20 μg/ml) from recombinant *C. sporogenes*. The results show that the cell extract from recombinant *C. sporogenes* expressing cytosine deaminase increases the cytotoxicity of 5-FC by a factor of $10^4$, bringing it to the same toxicity as 5-FU (larger closed circles) in the assay. Cell extract from *C. sporogenes* transformed with an empty vector did not affect the sensitivity of 5-FC (open squares), nor did cell extract from recombinant *C. sporogenes* affect sensitivity to 5-FU (smaller closed circles).

C. In vivo Expression of Cytosine Deaminase and Antitumor Activity

Figure 12:
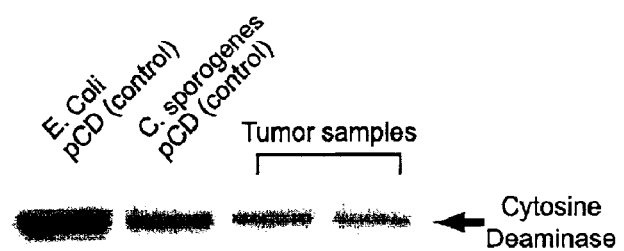
FIG. 12 is a Western blot analysis of cytosine deaminase protein expression in tumor homogenates prepared from in vivo tumors injected with spores of cytosine deaminase-transformed *C. sporogenes*. The two left lanes are controls of an *E. coli* transformed the cytosine deaminase vector [*E. coli* pCD (control)] and *C. sporogenes* transformed the CD vector [*C. sporogenes* pCD (control)].

The expression and activity of cytosine deaminase was evaluated in SCCVII tumors in mice, as described in Example 2. Tumor-bearing animals were injected with $10^8$ spores of recombinant *C. sporogenes*, prepared as described above. The tumors were excised 1–2 weeks later and samples prepared for immunoblot analysis of cytosine deaminase and for cytosine deaminase activity in vitro as judged by the ability to convert 5-fluorocytosine to a more toxic product. Western blots of homogenates of SCCVII tumors taken 14 days after injection of the cytosine deaminase-transformed *C. sporogenes* are shown in FIG. 12. The left panels are cell lysates transfected with vectors of cytosine deaminase-transformed *E. coli* and of cytosine deaminase-transformed *C. sporogenes* as controls. The two right panels FIG. 12 show that cytosine deaminase can be detected by immunoblot analysis in these tumors.

It was further demonstrated that incubating SCCVII cells with 5-FC plus tumor extract for two days resulted in an increase in cytotoxicity of 5-FC by a factor of approximately $10^3$.

Figure 13:
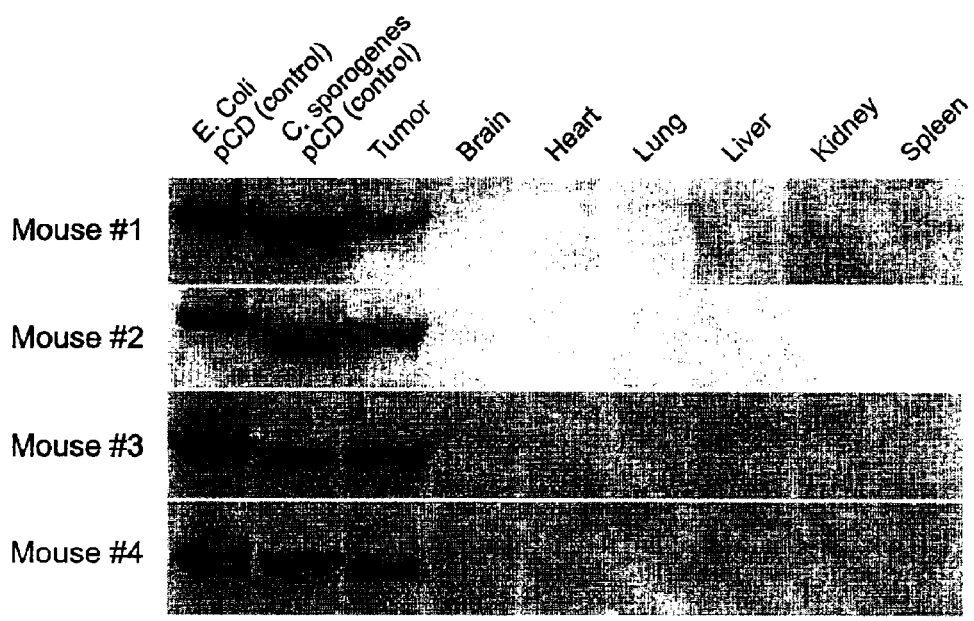
FIG. 13 is a Western blot analysis of cytosine deaminase protein expression in SCCVII tumors and several normal tissues (brain, heart, lung, liver, kidney, and spleen), taken from tumor-bearing mice after injection with recombinant spores of *C. sporogenes*. The two left lanes are controls of an *E. coli* transformed the cytosine deaminase vector [*E. coli* pCD (control)] and *C. sporogenes* transformed the CD vector [*C. sporogenes* pCD (control)].

In addition, SCCVII tumor-bearing mice were injected intraveneously with $10^8$ spores of recombinant *C. sporogenes*, followed by removal of the tumor, brain, heart, lung, liver, kidney, and spleen tissue seven days later. Immunoblot analysis was performed on equal amounts of protein from each of these tissue sources, and the results are shown in FIG. 13. The two left lanes in FIG. 13 correspond to cell extracts from cytosine deaminase-transformed *E. coli* and *C. sporogenes* as control. As seen in the blot, cytosine deaminase protein was confined to the tumor tissue, with no measurable cytosine deaminase protein found in the brain, heart, lung, liver, kidney, or spleen.

In another in vivo study, the ability of recombinant cytosine deaminase-expressing *C. sporogenes* to produce sufficient conversion of 5-FC to 5-FU in vivo to produce antitumor activity was evaluated. As described in Example 2C, tumor-bearing mice with an average tumor size 150 mg were injected with saline (control; open circles), 5-FC (open squares), 5-FU (closed triangles), recombinant spores alone on day 0 (closed squares), and recombinant spores one day prior to daily injections of 5-FC (closed circles). The results are shown in FIG. 13. The combination of 5-FC plus recombinant spores (closed circles) produced a similar or even greater delay in tumor growth than that produced by a maximum tolerated dose of 5-FU (closed triangles) given on the same schedule. The results establish the antitumor efficacy of tumor-specific targeting of an anticancer drug delivery system using an obligate anaerobe.

D. Persistence of Clostridial Colonization during Therapy

Figure 15:
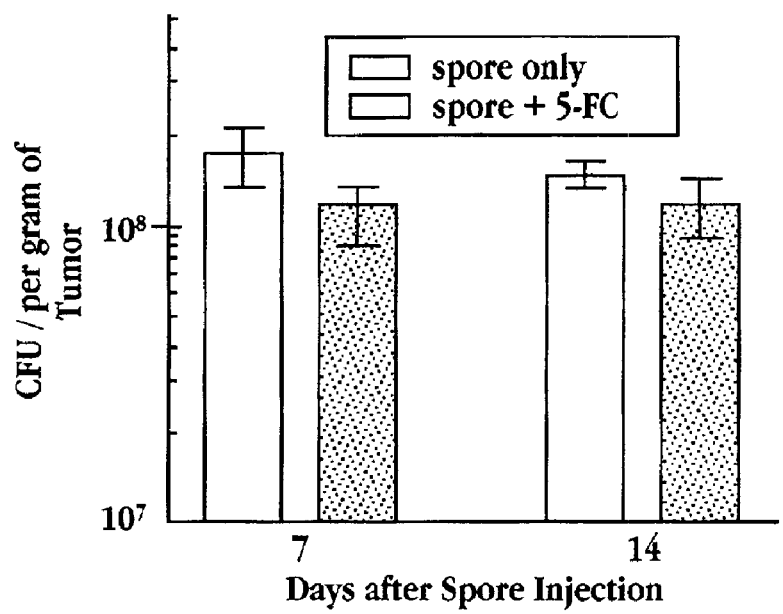
FIG. 15 shows the numbers of colony forming units (CFU) of vegetative cytosine deaminase-expressing C. sporogenes in SCCVII tumors at 7 and 14 days after a single injection of spores in mice treated for 2 weeks with saline or with 5-FC.

It has previously been observed that following transfection of tumor cells with prodrug-activating enzymes, the transduced cells may be rapidly and selectively killed and leave the population during therapy (Lawrence et al., 1998). If such rapid and selective killing were to take place, it would very difficult to give multiple treatments and particularly in the case of cytosine deaminase conversion of 5-FC to 5-FU, to maintain adequate levels of 5-FU as a radiosensitizer during fractionated radiotherapy (Lawrence et al., 1998). However, given that anticancer drugs are typically less active against microorganisms, it was hypothesized that this would not be a problem. This was confirmed by measuring the number of clostridial colony-forming units (CFU) per gram of tumor on day 7 and day 14 after administering spore alone or spores plus 5 times per week injections of 5-FC (500 mg/kg/day). As can be seen in FIG. 15, there was no significant difference between the two groups, and levels of clostridial CFUs were undiminished at day 14 as compared to day 7.

The studies described herein demonstrate the effective expression of recombinant enzymes that are capable of converting prodrugs into chemotherapeutic agents by recombinant *Clostridium* bacteria. A high level replication of viable *clostridia* in the hypoxic environment of solid tumors resulting in localized expression of the recombinant enzyme nucleic acid was achieved, along with a corresponding localized conversion of the prodrug into the active chemotherapeutic agent. The studies also show a significant antitumor efficacy of systemically injected 5-fluorocytosine following injection of recombinant spores. This demonstrates that systemically administered recombinant *Clostridium* can be used to achieve tumor specific expression of a prodrug-activating enzyme resulting in anti-tumor activity.

III. Tumor Treatment Strategies

In order to improve the efficacy of current chemotherapeutic treatment and diminish side effects, prodrug strategies have evolved in an attempt to achieve site-specific delivery of cytotoxic anticancer agents. This strategy is based on the relative lack of toxicity of prodrugs in comparison to their anticancer (chemotherapeutic) drug counterparts. Such strategies often take advantage of differences between tumor cells and "normal" healthy cells, based on tumor-associated factors, such as hypoxia, tumor-associated enzymes and receptors.

Human solid tumors, which make up more than 90% of all human cancers are known to comprise a hypoxic environment. This leads to resistance to radiotherapy and anticancer chemotherapy, as well as predisposing to increased tumor metastases (Gray et al., 1953; Hockel et al., 1996; Brizel et al., 1996).

Recent cancer treatment strategies have focused on the differences between tumor cells and normal healthy cells in drug targeting. It is generally known in the art that oxygen deficiency in the core of solid tumors leads to enhanced activity of reducing enzymes, e.g., nitroreductases, which can be used for site-specific conversion of prodrug to drug.

Hypoxia is unique for human solid tumors and non-pathogenic spore-forming anaerobic bacteria of the genus *Clostridium* have been used experimentally as anti-cancer agents because of their selective germination and proliferation in hypoxic regions of solid tumors after systemic injection of the inactive spore form of the bacteria. The present invention takes advantage of the unique properties of tumor cells in tumor-specific enzyme/prodrug gene therapy using genetically engineered species of anaerobic organisms, exemplified herein by species of *Clostridia*. In a preferred embodiment of the present invention, the clostridial strain is designated as *Clostridium sporogenes, Clostridium oncolyticum* or *Clostridium butyricum* strain (later renamed *C. oncolyticum*).

Any of a number of non toxic prodrugs may be converted to a toxic chemotherapeutic agent by the action of an enzyme. Exemplary enzymes that may be used to convert a prodrug into the form of an active chemotherapeutic agent include, but are not limited to, cytosine deaminase, nitroreductase, β-glucuronidase, β-galactosidase, a carboxypeptidase, alkaline phosphatase and β-lactamase. See, e.g., Melton et al., 1996.

For example, β-glucuronidase may be used to convert prodrugs comprising glucuronides such as epirubicin, doxorubicin, or 4-hydroxycyclophosphamide into forms which are active chemotherapeutic agents.

Some examples of such prodrugs and corresponding toxic chemotherapeutic agents include the following:

A. Nitroreductase with CB1954

CB1954 as used herein refers to the monofunctional alkylating agent (5-[aziridine-1-yl]-2,4-dinitrobenzamide) and to analogues thereof (Wilson et al. 2002). The compound was synthesized almost 25 years ago and shown to have potent activity against the Walker 256 rat carcinoma in vivo (Cobb et al. 1969) and on Walker carcinoma cells in vitro (Roberts et al., 1986). However, it has been shown to exhibit poor activity against a range of mouse and human tumor cell lines (Boland et al., 1991; Workman et al., 1986). The extreme toxicity of the drug to Walker tumor cells was demonstrated to result from its conversion to a bifunctional alkylating agent which caused DNA interstrand crosslinks in these cells (Roberts et al., supra). Subsequently, the toxic bifunctional alkylating agent was identified as the 4-hydroxylamine metabolite of CB1954, which was formed by a DT-diaphorase enzyme in Walker carcinoma cells (Knox et al., 1988). The difference in sensitivity between rat and human cells (a factor of $10^4$–$10^5$) was shown to be the result of differences in the rates of reduction of CB1954 by rat and human DT diaphorases: the human form of DT diaphorase is intrinsically less able to reduce the compound than the rat form (Boland et al., supra).

The 4-hydroxylamine toxic metabolite can be formed in one cell and can freely diffuse to produce cytotoxicity in another, as demonstrated by Knox et al., 1988). It has been shown that the toxic metabolite can diffuse through clostridial cell walls and, therefore, the toxic species can be formed within the nitroreductase-expressing recombinant. This obviated the need for external NADH or NADPH co-factors, since *C. acetobutylicum* possesses both of these electron donors (Petitdemange et al., 1976). This is an advantage over the ADEPT approach, in which the enzyme is located outside of the cell requiring application of the co-factor. The nitroreductase enzyme is also found in the supernatant of recombinant *C. acetobutylicum*, demonstrating that the recombinant enzyme is present within and outside the bacteria.

One enzyme particularly preferred for expression in recombinant *Clostridium*, is the nitroreductase enzyme from *E. coli* which was recently isolated and shown to reduce CB1954 at a rate 60 times greater than that of the rat DT diaphorase. (Anlezark et a., 1992).

B. β-Glucuronidase with Glucuronidated Anticancer Drugs

The glycosidase β-glucuronidase occurs in both prokaryotic and eukaryotic organisms. Its concentration in human serum is very low (Stahl et al., 1984), and, therefore, glucuronide prodrugs are relatively stable in blood following IV administration. Indeed, the conjugation of xenobiotics, including anticancer drugs, with glucuronide is a major route by which such drugs are eliminated (Connors et al., 1971–1980, 1973; Maftouh et al. 1984; Weenen et al., 1984).

Wang et al., 1992 conjugated β-glucuronidase from *E. coli* to MAb RH1, a murine IgG that binds strongly to rat hepatoma cells, but not to human hepatoma cells. As a prodrug they tested a butylated ammonium salt of the glucuronide conjugate of hydroxyanaline mustard. They found that the prodrug was $10^3$ times less potent than hydroxyanaline mustard (HAM) and showed that when β-glucuronidase, either free or conjugated to the MAb, was added to the prodrug, it became as toxic as the nonglucuronide form, HAM. See also, Haisma et al., 1992 who conjugated *E. coli*-derived β-glucuronidase to the anti-pan carcinoma, MAb 323/A3. As a prodrug, they used the glucuronide conjugate of epirubicin, an anticancer agent used in patients with breast cancer, lymphomas, ovarian cancer, and soft tissue sarcomas. They showed that the prodrug was approximately 100-fold less toxic to human breast and ovarian cancer cells, but became as toxic as epirubicin when combined with a Mab-β-glucuronidase conjugate.

A doxorubicin prodrug (N-[4-doxorubicin-N-carbonyl (oxymethyl) phenyl] O-beta-glucuronyl carbamate) has also been described for specific activation by human β-glucuronidase or β-galactosidase, which are released in necrotic areas of tumor lesions (Houba et al., 1999; Houba et al., 2001; Leenders et al., 1999).

C. Cytosine Deaminase and 5-Fluorocytosine

5-Fluorouracil, an antimetabolite, has been in clinical use since 1957. Sensitive tumors include breast cancer, gastrointestinal malignancies, and cancers of the head and neck. Topical administration is useful for basal cell carcinomas and other malignant dermatoses. Metabolism of 5-fluorouracil produces two critical intermediates: fluoro-uridine-5′-phosphate (FUTP), which is incorporated into RNA and interferes with its function, and fluoro-deoxyuridylate (FdUMP) which prevents normal DNA replication. However, the clinical effectiveness of 5-Fluorouracil and related compounds has been limited by toxicity, particularly evident in the bone marrow.

The 1-N-β-glucuronide of 5-fluorouracil has been synthesized (Alexander et al., 1991; Kulinkovich et al., 1983) and shown to be stable in vivo (Germane et al., 1987). It is cleaved to 5-fluorouracil by β-glucuronidase.

Cytosine deaminase catalyzes the deamination of cytosine to uracil. Mammalian cells do not ordinarily produce this enzyme, whereas many bacteria and fungi do. Microorganisms that express cytosine deaminase can convert 5-fluorocytosine to 5-fluorouracil, a highly toxic metabolite that has potent cytotoxic effects on mammalian cells and is widely used as a cancer chemotherapeutic agent (Mullen et al., 1992).

The enzyme/prodrug combination of cytosine deaminase/5-fluorocytosine has been explored using antibody-directed enzyme prodrug therapy (ADEPT) and virus-directed enzyme prodrug therapy (VDEPT) approaches, but has met with limited success (Fox et al., 1996).

D. Proteases

The invasive and metastatic activities of tumor cells provide a need for tumor-associated proteases, e.g., plasmin. Prodrugs of daunorubicin and doxorubicin designed for selective activation by the serine protease plasmin have been described (de Groot et al., 2000 and de Groot et al., 1999).

In addition, at least two carboxypeptidases have been used to convert a prodrug into a chemotherapeutic agent, e.g. the conversion of methotrexate-α-alanine to methotrexate (Vitols et al., 1989; Vitols et al., 1995). See, also Niculescu-Duvaz et al., 1999, which describes the use of carboxypeptidase G2 in a gene-directed enzyme prodrug therapy (GDEPT) system for use in the conversion of nitrogen mustard prodrugs into the corresponding active form. Carboxypeptidase G2 finds utility in the cleavage of amidic, urethanic or ureidic bonds between a benzene nucleus and L-glutamic acid.

E. Alkaline Phosphatase

Alkaline phosphatase may be used to remove the phosphate group from inactive prodrugs converting them into chemotherapeutic agents. For example, alkaline phosphatase has been used in the conversion of etoposide phosphate, doxorubicin phosphate and mitomycin C phosphate into etoposide, doxorubicin and mitomycin C, respectively (Senter et al., 1989).

F. β-Lactamase

The use of antibody-directed catalysis (ADC) for the delivery of a cephalosporin derivative of the oncolytic agent 4-desacetylvinblastine-3-carboxyhydrazide conjugated to F(ab')-β-lactamase conjugates exhibiting both β-lactamase activity and immunoreactivity toward carcinoembryonic antigen (CEA) was shown to have potential for immunochemotherapy in preclinical models (Meyer et al., 1993).

IV. Expression of Recombinant Enzymes in Anaerobic Bacteria

The present invention is based on transformation of bacteria with recombinant expression vectors effective to express an enzyme capable of converting a prodrug into a toxic chemotherapeutic agent, particularly in obligate anaerobes of the genus *Clostridia*.

It will be understood that while particular enzyme prodrug combinations are exemplified herein, the invention contemplates expression vectors comprising the coding sequence for any of a number of enzymes capable of converting a prodrug into a toxic chemotherapeutic agent so long as the enzyme can be expressed in *Clostridium sporogenes* (of which *C. oncolyticum*, previously known as *Clostridium butyricum*, is a member).

Exemplary enzymes include, but are not limited to cytosine deaminase, nitroreductase, β-glucuronidase, β-galactosidase, a carboxypeptidase, alkaline phosphatase and β-lactamase.

A. Enzyme-Encoding Nucleic Acid Sequences.

Accordingly, although specific enzyme-encoding nucleic acid sequences are exemplified herein, the invention includes homologues of the exemplified coding sequences isolated from other species, naturally occurring allelic and splice variants, nucleic acid fragments, and biologically active (functional) derivatives thereof, such as, nucleic acid sequences that encode amino acid sequence variants of the native enzyme and sequences which encode fusion proteins, so long as the enzyme maintains its biological activity (the ability to convert a prodrug into a toxic chemotherapeutic agent).

Due to the inherent degeneracy of the genetic code, nucleic acid sequences other than the native form, such as the *E. coli* cytosine deaminase sequence presented at GenBank Accession No. S56903, and which encode substantially the same or a functionally equivalent amino acid sequence may be used to clone and/or express cytosine deaminase in *Clostridium sporogenes*. Thus, for a given enzyme-encoding nucleic acid sequence, it is appreciated that as a result of the degeneracy of the genetic code, a number of coding sequences can be produced that encode a protein having the same amino acid sequence. For example, the triplet CGT encodes the amino acid arginine. Arginine is alternatively encoded by CGA, CGC, CGG, AGA, and AGG. Therefore it is appreciated that such substitutions in the coding region fall within the nucleic acid sequence variants covered by the present invention. Any and all of these sequence variants can be utilized in the same way as described herein for the native form of the nucleic acid sequence that encodes an enzyme capable of converting a prodrug into a toxic chemotherapeutic agent when expressed in an obligate anaerobe.

In general, the coding sequence for particular enzymes that are effective in converting a prodrug into a chemotherapeutic agent and are therefore useful in practicing the present invention may be found in GenBank or in the scientific literature. Such enzymes may be found in one or more forms and may be isolated from one or more species. By way of example, the *E. coli* cytosine deaminase sequence may be found at GenBank Accession No. S56903 and a yeast derived form of cytosine deaminase may be found at GenBank Accession No. GenBank Accession No. U55194. Either of these coding sequence may be incorporated into an expression vector for transformation into *Clostridium* spp. in practicing the present invention. While both sequences may be effective to express cytosine deaminase in recombinant *Clostridium*, it will be understood that in some cases different coding sequences for the same enzyme may result in different expression levels of a biologically active form of the enzyme. See, e.g., Hamstra et al., 1999.

In one general embodiment, such sequence variants have at least 70%, preferably 80%, 85%, 90%, 95%, 98%, or more sequence identity to the coding sequence for a native form of the enzyme.

In another embodiment, the enzyme-encoding nucleotide sequence will hybridize under moderate to high stringency conditions to a nucleotide sequence that encodes a native form of the enzyme.

As will be further understood by those of skill in the art, in some cases it may be advantageous to produce nucleotide sequences possessing non-naturally occurring codons. Codons preferred by a particular host can be selected, for example, to increase the rate of protein expression or to produce recombinant RNA transcripts having desirable properties, such as a longer half-life, than transcripts produced from the naturally occurring sequence. Hence, a native enzyme-encoding nucleotide sequence may be engineered in order to alter the coding sequence for a variety of reasons, including but not limited to, alterations which modify the cloning, processing and/or expression of the enzyme by an anaerobic bacterial cell, e.g., a *Clostridium* bacteria.

Particularly preferred are nucleic acid substitutions, additions, and deletions that are silent such that they do not alter the properties or activities of the enzyme following expression in recombinant bacteria.

The variations can be made using methods known in the art such as oligonucleotide-mediated (site-directed) mutagenesis, alanine scanning, and PCR mutagenesis. Site-directed mutagenesis [Carter et al., 1986; Zoller et al., 1987], cassette mutagenesis [Wells et al., 1985], restriction selection mutagenesis [Wells et al., 1986] or other known techniques can be performed on the cloned DNA to produce the enzyme-encoding variant DNA.

B. Vectors for Transformation of *Clostridium* spp

Vectors for transformation of *Clostridium* spp. were constructed using the *E. coli Clostridium* shuttle vectors, pMTL500F and pMTL500FT (Minton et al., 1981). These shuttle vectors are based on the previously constructed *E. coli* cloning vector, pMTL500E (Oultram et al., 1988). The promoter and RBS of the lacZ' were replaced in pMTL500F by the equivalent signals of the ferredoxin (Fd) gene of *Clostridium pasteurianum*.

Since the promoter elements and ribosome binding sites of Gram-negative bacteria are generally poorly utilized in Gram-positive bacteria, preferred vectors for practicing the present invention include the multiple cloning site (MCS) placed 3' to the promoter and RBS of *Clostridium pasteurianum*, such that heterologous genes inserted into the MCS are efficiently expressed in both Gram-positive and Gram-negative bacteria. Such vectors are preferred for the expression of the nucleic acid sequence encoding an enzyme capable of converting a prodrug into a chemotherapeutic agent in *Clostridium* spp., in particular in *Clostridium sporogenes*. An Nde1 site is the first restriction site of the MCS and serves as the insertion site for the coding sequence the enzyme.

The methods of the invention rely on the use of anaerobic *Clostridium* cultures to express an enzyme capable of converting a prodrug into a toxic chemotherapeutic agent, in particular in *Clostridium sporogenes*, with no particular method of enzyme expression required. In this aspect, the invention provides *Clostridium* host cells that have been transduced, transformed or transfected with an expression vector comprising an enzyme-encoding nucleic acid sequence. The culture conditions, such as temperature, pH and the like, are those previously used for the culture of the bacteria prior to transduction, transformation or transfection and will be apparent to those skilled in the art.

Various methods may be employed for delivering the expression vector into bacterial cells in vitro. Methods of introducing nucleic acids into bacteria include, but are not limited to, electroporation; microinjection; bacterial protoplast fusion with intact cells; use of polycations, e.g., polybrene or polyornithine; membrane fusion with liposomes, lipofectamine or lipofection-mediated transfection; high velocity bombardment with DNA-coated microprojectiles; incubation with calcium phosphate-DNA precipitate; DEAE-Dextran mediated transfection; infection with modified viral nucleic acids; and the like. In a preferred embodiment of the present invention, electroporation is carried out under the conditions specified in Example 2.

V. Methods of Detecting Gene Expression

In order to evaluate the expression of an enzyme by bacterial cells that have been transformed with an expression vector such as described herein, assays can be carried out at the protein level, the RNA level and/or by use of functional bioassays particular to the activity of the enzyme expressed by the recombinant bacteria.

Such assays include Northern blotting to quantitate the transcription of mRNA, dot blotting (DNA or RNA analysis), RT-PCR (reverse transcriptase polymerase chain reaction), or in situ hybridization, using an appropriately labeled probe (based on the nucleic acid coding sequence) and conventional Southern blotting.

Alternatively, protein expression may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of a given enzyme. Exemplary methods are briefly described below, given that such methods are generally known to those of skill in the art and many reagents for practicing the methods are commercially available.

A purified form of the enzyme expressed by the recombinant bacteria may be used to produce either monoclonal or polyclonal antibodies specific to the expressed protein for use in various immunoassays. (See, e.g., Harlow et al., 1988). Exemplary assays include ELISA, competitive immunoassays, radioimmunoassays, Western blot, indirect immunofluorescent assays and the like. In many cases, commercially available antibodies and/or kits may be used for immunoassay of the enzyme.

(A) Enzyme Activity Assays

ELISA Assays for Recombinant Proteins

Levels of enzymes, e.g., cytosine deaminase, nitroreductase, β-glucuronidase, β-galactosidase, carboxypeptidase, alkaline phosphatase or β-lactamase and clostridial cell wall proteins may be determined in tumor tissue, plasma, and normal host tissue using an ELISA technique. In order to maximize the sensitivity of the assay, a non-competitive homogeneous sandwich ELISA assay such as that described by Noe et al., 1992, is typically used.

Briefly, in one exemplary assay format, rabbit polyclonal antibodies raised against the purified enzyme or clostridial cell wall extract is adsorbed onto 96-well plates. Serially diluted samples of plasma, cell lysates, or standards consisting of a purified form of the protein are then added to the wells. After allowing for the antigen to bind to the immobilized antibody, the wells are washed repeatedly to remove unbound protein. A biotinylated anti-enzyme polyclonal antibody is then added to the well and allowed to react with the immobilized antigen. Avidin and biotinylated alkaline phosphatase are then added, the wells are washed, and the signal quantified by adding p-nitrophenyl phosphate and reading the absorbance at 405 nm using a 96-well plate reader.

In another exemplary type of assay, β-Glucuronidase activity is measured in cultures of *Clostridium* spp. using the spectrophotometric method described by Fishman, W. H., "β-Glucuronidase" in: METHODS OF ENZYMATIC ANALYSIS (Weinheim: Verlag Chemie, Bergmeyer, H. U. and K. Gawehn, eds. 1974). Plasma or crude cell homogenates are incubated in acetate buffer pH 4.0 with 8 mM 4-nitrophenyl-β-D-glucuronoside and monitored continuously at 405 nm for the release of 4-nitrophenol ($\epsilon_{405}=18.5$ mmol$^{-1}$cm$^{-1}$). The slope of the absorbance curve is used to calculate enzymatic activity. One unit of β-glucuronidase activity is defined as the release of 1 umol 4-nitrophenol per min at 25 C and pH 4.0.

Similarly, nitroreductase activity may be measured in cultures of *Clostridium* spp. using a modification of the method developed by Gordon et al., 1991. Briefly, samples diluted in 25 mM Tris-HCl buffer containing 0.7 mg/ml bovine serum albumin are placed in an assay mixture containing 4 µM dichlorophenol-indophenol (DCIP) and 200 µM NADH, and the rate of DCIP reduction is followed spectrophotometrically at 600 nm. Replicate samples containing 50 µM dicoumoral, a potent inhibitor of nitroreductase, are used to correct for nonspecific DCIP reduction. Protein concentrations are measured with a BCA Protein Assay Kit method (Pierce) utilizing bovine serum albumin as a standard.

(B) In vivo Assays

C3H/Km mice are typically used for transplantation of RIF-1 and SCCVII/St mouse tumors; BALB/c are typically used for transplantation of EMT6/St tumors; and SCID mice are typically used for transplantation of the HT 29 human tumor. Normal tissue studies are generally performed on C3H/Km mice. It will be understood that alternative strains of mice may be used so long as the tumor cells under investigation grow in the host animal.

Rodent tumors have been used extensively over the past 5–20 years (depending on the tumor), and rigorous procedures have been established for passage of the cells from frozen tumor characteristics. A full description of this is given for the RIF-1 tumor (Twentyman et al., 1980), and an identical practice is used for the other tumors. Full descriptions of the derivation, characteristics and handling of the rodent tumors are known in the art. (See for example, Brown et al., 1979; Brown et al., 1981; Hirst et al., 1982; Rockwell et al., 1972).

In vivo assays for anti-tumor activity may be based on any assay that provides information on the effect of a particular treatment on tumor growth. For example, an assay such as a regrowth delay assay may used to evaluate the effect of a particular treatment on the ability of a tumor to regrow in vivo in an animal. Regrowth assays may be performed using any tumor that will grow in an animal, e.g., an SCCVII/St, RIF-1 or HT 29 tumor. After treatment, tumor volumes are measured and the time required for a tumor to regrow to a size equal to 2 or 4 times the tumor volume at the time of treatment is evaluated. (See, e.g., Brown J M, 1975; Brown et al., 1982; Brown et al., 1990; Brown et al., 1979; Stone et al., 1991).

Another exemplary type of assay is a tumor control ($TCD_{50}$) assay, which is based on the dose of a compound that results in tumor control in 50% of treated mice (the $TCD_{50}$). After treatment tumors are measured at regular intervals. In one example of this approach, after treatment tumors are measured at weekly intervals, until they exceed 4× the treatment volume or reach 120 days post-treatment. At this time, the mice are sacrificed and autopsied. A mouse is recorded as "cured" if at 120 days post-treatment it does not have a tumor greater than 4 mm mean diameter. (See, e.g., Brown et al., 1981; Brown et al., 1979; Stone et al., 1991). This assay has been used in testing the MDAH/MCa4 carcinoma and RIF-1 sarcoma and has been applied to the SCCVII, RIF-1 mouse tumors and the HT 29 human tumor.

VI. Utility

The invention described herein presents a method for specific and effective delivery of a chemotherapeutic agent to a tumor. The invention provides compositions and methods for high level expression of a prodrug-activating enzyme, together with bacteria capable of high capacity proliferation in the tumor microenvironment, resulting in a tumor-specific gene delivery system which has widespread utility to treatment of cancers that manifest as solid tumors.

Specific examples are described herein, however, it will be apparent to one of ordinary skill in the art that many modifications are possible and that the examples are provided for purposes of illustration only and do not limit the invention, unless so specified.

All patent and literature references cited in the present specification are hereby incorporated by reference in their entirety.

VII. EXAMPLES

The following examples further illustrate the invention described herein and are in no way intended to limit the scope of the invention.

Materials and Methods

A. Mice and Tumors

C3H/Km mice were used for transplantation of RIF-1 and SCCVII/St mouse tumors; BALB/c were used for transplantation of EMT6/St tumors; and SCID mice were used for transplantation of the HT 29 human tumor. Normal tissue studies were performed on C3H/Km mice. All the mice were bred and housed within the new Research Animal Facility at Stanford University. All the tumors were assayed for cell survival in vitro by plating single cells into petri dishes.

B. Growth and Sporulation of *Clostridium* spp is carried out using routine conditions generally applied by those of skill in the art, with no particular method of culture required.

Sporulation cultures were typically started from exponentially growing cultures. Spores were typically stored at 4° C. until needed for animal injection. Spores were injected intravenously into mice in 0.1 ml volume from spore suspensions in PBS of $10^9$ spores/ml.

C. Electrophoresis and Immunoblotting

SDS-PAGE one dimensional electrophoresis was carried out using 12% gels (Laemmli, U K, 1970). Following electrophoresis, protein was transferred to nitrocellulose sheets using a Bio-Rad semi-dry blotter at 25 V for 1 hr using the buffer system of Towbin et al., 1979. Immunoblotting was typically performed using polyclonal antibody preparations derived from rabbits and directed against *E. coli* cytosine deaminase, nitroreductase, or β-glucuronidase.

By way of example, nondenaturing polyacrylamide gel electrophoresis was performed by the method of Davis using 10% slab gels in a Bio-Rad Mini-Protein II apparatus (Davis, J. B., 1964). Nitroreductase activity was visualized by a modification of the method of Kaplan and Beutler used to measure glutathione reductase (Kaplan et al., 1968). When oxidized glutathione was omitted from the assay mixture, this method detects both DT diaphorase and nitroreductase. These two enzymes were easily differentiated by their different electrophoretic mobilities.

D. Polyclonal Antibody Production

Antibodies against the enzyme expressed in recombinant anaerobes in order to convert a prodrug to its chemotherapeutic counterpart, e.g., cytosine deaminase, nitroreductase, or β-glucuronidase, were used for immunoassays and immunohistochemistry, etc. to visualize the localization of expressed recombinant enzyme in tumor and tissue slices. An antibody to crude whole-*clostridia* homogenate was produced for use with immunohistochemistry methods to augment traditional staining methods designed to detect both vegetative and spore forms of *clostridia* in tissue and tumor sections. Polyclonal antibodies for use in immunohistochemistry, immunoblotting, and ELISA assays were produced in rabbits using a modification of the technique published by Oberley et al., 1990. Due to the bacterial origin of the antigens, prior to immunization, the antigen preparations were rendered endotoxin-free by passing them over a lipid A-binding affinity matrix (Detoxi-Gel, Pierce). This procedure also utilized Ribi adjuvant instead of Freund's complete and incomplete adjuvant to minimize animal discomfort.

Example 1

Expression of the *E. coli* ntr Gene in *Clostridium* spp

A. Construction of Vectors for Expression of Nitroreductase

The gene (ntr) encoding *E. coli* B nitroreductase (NTR) was cloned and its nucleotide sequence determined. The fragment characterized was shown to carry the ntr promoter in addition to the structural gene. The transcriptional initiation signals and the ribosome binding sites (RBS) from the gram-negative *E. coli* were replaced with Gram-positive equivalents, as follows.

Figure 4:
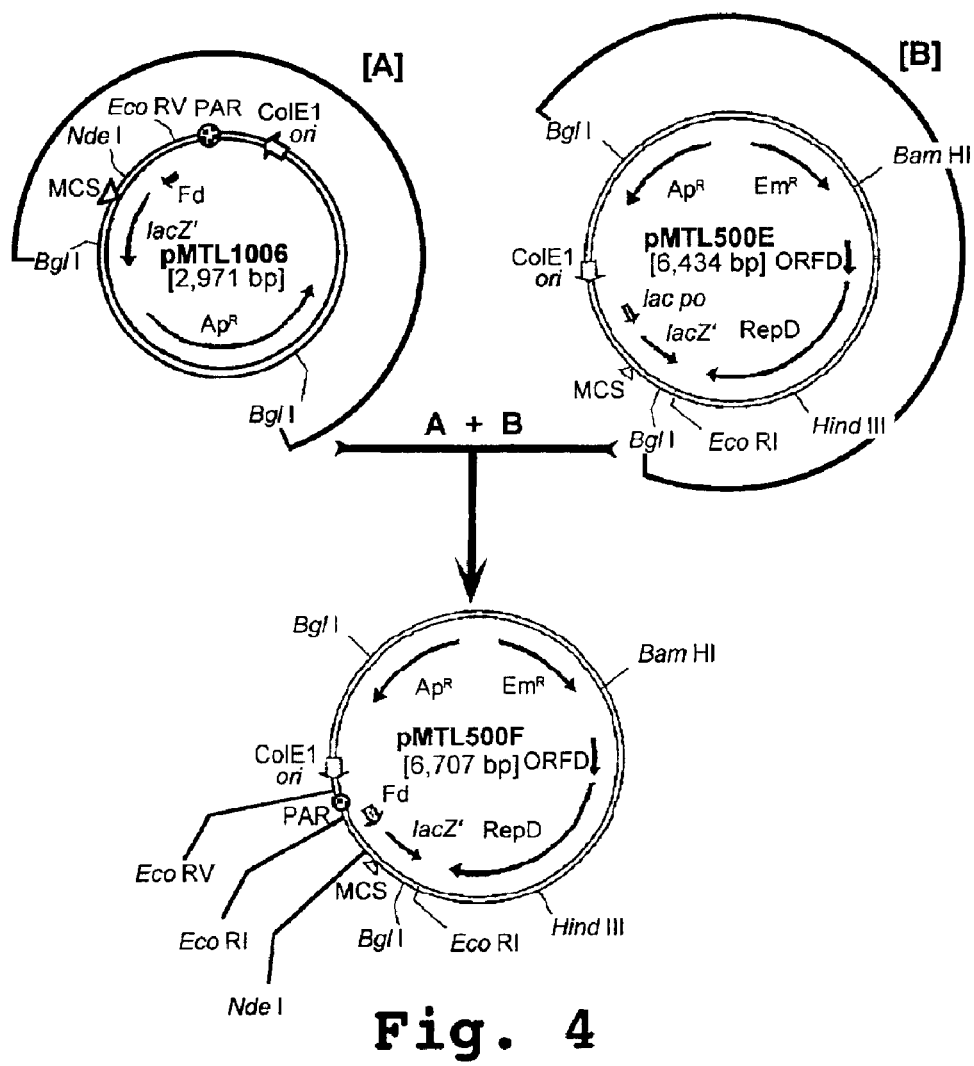
FIG. 4 illustrates the construction of the expression vector pMTL500F. Following cleavage of pMTL1006 and pMTL500E with BglI, the indicated fragments (A and B) were isolated from the respective plasmids and ligated together to give plasmid pMTL500F. Key: Em=erythromycin; lac po=the promoter/operator region of the *E. coli* lac operon.

Based on the previously constructed *E. coli Clostridium* cloning vector, pMTL500E (Oultram et al), the promoter and RBS of the lacZ' were replaced in pMTL500F by the equivalent signals of the ferrodoxin (Fd) gene of *Clostridium pasteurianum*, as illustrated in FIG. 1. A 604 bp MboI fragment carrying the *Clostridium pasteurianum* ferrodoxin gene was isolated from the genome of strain ATCC 6013 and cloned into the BamHI site of M13mp7. The nucleotide sequence of the cloned fragment was found to be identical to that reported by Graves et al., 1985. Site-directed mutagenesis was used to change the triplet immediately preceding the translational start codon from TTC to CAT, thereby creating a recognition sequence for the restriction enzyme NdeI. A unique HpaI site was also created within the promoter region by changing nucleotide position 132 from "A" to "T" (Graves et al., 1985). Into this created site, a 25 bp blunt-ended, synthetic DNA fragment corresponding to the operator of the *E. coli* lac promoter was inserted. The modified Fd promoter was subsequently isolated as a 200 bp fragment, as shown in FIG. 2 (SEQ ID NO:1), following cleavage with NdeI and EcoRI, and cloned between the equivalent sites of the expression vector pMTL1003 (Brehm et al., 1991) to give PMTL1006, as shown in FIG. 3. The final step involved replacing the lac promoter of pMTL500E with the Fd promoter of pMTL1006. This was achieved by combining a 1.871 Kb BglI fragment isolated from pMTL 1006 with a 4,839 Kb BglI fragment isolated from pMTL500E, as shown in FIG. 4. The resulting plasmid was designated pMTL500F.

A recombinant plasmid capable of directing the expression of the *E. coli* nitroreductase (ntr) gene in *C. acetobutylicum* (later renamed *C. beijerinkii*) was constructed as illustrated in FIG. 1. In essence, a Nde1 site was created 'over' the translational start codon of the ntr gene allowing its subsequent insertion into pMTL500F immediately adjacent to the clostridial Fd promoter and ribosome binding site. Two oligonucleotide primers were employed to amplify a 700 bp fragment carrying the *E. coli* nitroreductase gene. Simultaneously, primer 1 created an Nde1 site. The amplified fragment was subsequently inserted between the Nde1 and Pst1 sites of the expression vector pMTL500F. In the resulting recombinant, pNTR500F, the ntr gene was under transcriptional and translational control of the promoter (Fd) and ribosome binding site, respectively, of the *C. pasteurianum* ferrodoxin gene. Ap' and Em' are ampicillin and erythromycin resistance genes, respectively. RepD and RepE are pAMβ1-derived replication proteins, and ORI is the replication origin of ColE1.

pNTR500F was transformed into *B. substilis* and *C. acetobutylicum* NCIMB 8052, using electroporation (Oultram, 1988).

B. Nitroreductase (NTR) Activity in vitro

To quantify the expression of the recombinant *E. coli* nitroreductase in bacterial cultures, a spectrophotometric enzyme activity assay was used to measure nitroreductase activity in the supernatant and cell pellet fractions of transformed Clostridial cultures. This assay, based upon the reduction of dichlorophenol-indophenol in the presence of NADH, demonstrated that *Clostridia* transformed with the plasmid containing the *E. coli* ntr gene (pNTR500F) exhibited a 200-fold increase in NTR activity when compared to the endogenous activity of the parental wild-type strain in mid-log phase cultures (44 U/mg protein in culture supernatants for transformed *C. acetobutylicum* vs. 0.2 U/mg for the parental strain). In early log phase cultures, total nitroreductase activity was low (4 U/mg protein) and greater than 95% enzymatic activity was associated with the cell pellet. As cultures progressed into stationary phase, nitroreductase activity accumulated within the culture media and was increasingly found in the supernatant fraction. By 24 hours post-inoculation, total nitroreductase activity within the culture had risen to 105 U/mg protein, and 95% of the activity was associated with the supernatant fraction of the culture.

*E. coli* NTR activity was visualized in nondenaturing polyacrylamide gels. FIG. 5A is an artists rendering of the gel after staining for NTR activity, where the lanes were loaded with Clostridial lysate alone or EMT6 tumor lysate alone or with a mixture of the two. The mixtures were prepared by mixing 50 μg of EMT6 tumor lysate with decreasing amounts (5 μg to 250 ng) NTR-transformed *C. acetobutylicum*. The test mixtures were run on a native gel and then stained for NTR activity. Both bacterial NTR and mammalian DT-diaphorase were detected by the staining, however, the different electrophoretic mobilities of the two enzymes allowed NTR activity from as little as 250 ng *C. acetobutylicum* lysate to be easily visualized in the presence of a 200-fold excess of EMT6 protein.

Western blotting was also used to detect recombinant NTR in tumor lysates. FIG. 5B shows an artists rendering of a blot, stained with anti-*E. coli* NTR antibody, containing EMT6 tumor samples removed four days following i.v. injection of saline, wild type *C. acetobutylicum* spores, or spores from NTR-transformed bacteria into tumor bearing mice. The antibody detects protein of approximately the appropriate size (27 kD) and mobility of the NTR protein standard in the two samples derived from tumors injected with spores expressing recombinant NTR. NTR protein is not detectable in tumor samples derived from animals injected with saline or wildtype *C. acetobutylicum*. An additional protein (77 kD) was also detected by this antibody in all tumor samples. This blot demonstrates that *C. acetobutylicum* spores are vectors capable of expressing recombinant proteins in vivo and that these recombinant proteins can be detected in tumor homogenates.

Recombinant *E. coli* nitroreductase was partially purified from transformed *C. acetobutylicum* using a modification of the affinity chromatography technique of Ysern and Prochaska. A preliminary isolation yielded a 100-fold purification of nitroreductase in a single affinity chromatography step from a clarified homogenate of *E. coli* expressing the nitroreductase plasmid. The homogenate was passed over a dye affinity column (Affi-Gel Blue, Bio-Rad) and washed with increasing concentrations of NaCl. A highly enriched nitroreductase fraction was eluted from the column in a 1 M NaCl wash. Denaturing polyacrylamide gel electrophoresis of the eluted fraction followed by silver staining demonstrated at least four strongly staining protein bands. The major constituent was estimated to have a molecular weight of 26.5 kDa, very close to the reported size of 24 kDa for *E. coli* nitroreductase (Anlezark et al.). Further purification steps produced a preparation of sufficient purity to use as antigen for antibody production and standards in the ELISA assay, native gel electrophoresis, and immunoblotting assays.

In order to test the ability of recombinant *C. acetobutylicum* to activate CB1954, recombinant and wild type *C. acetobutylicum* were inoculated into 20 ml of medium. After overnight incubation, the cultures were centrifuged and the supernatant collected and diluted 1:3 with Waymouth's growth medium. This mixture, which had a pH of approximately 6.9, was then transferred to 60 mm, plastic petri dishes containing SCCVII tumor cells, which were approximately 50% confluent. To these cultures, different concentrations of CB1954 in DMSO were added, and the amount of DMSO adjusted in all of the cultures (including the controls) to 1% DMSO. Controls consisted of cell culture with only the supernatant/cell culture medium mixture. All plates received NADH to a final concentration of 500 µM.

After a 2 hr incubation in air at 37° C., the medium was removed, all the plates were washed 3 times with PBS, trypsinized, the cells counted by hemocytometer, and appropriate dilutions plated and incubated for 10 days in a 5% $CO_2$ incubator at 370 C for colony growth. The results are presented in FIG. 6, and show supernatant from the transformed *C. acetobutylicum* was capable of enhancing the toxicity of CB1954 by approximately 10-fold.

C. Nitroreductase Activity in vivo

In vivo studies with three different transplanted mouse tumors, EMT6, SCCVII and RIF1 tumors, and with human colon carcinoma HT29 transplanted into immune-deficient SCID mice were performed. Tumors were injected with spores of control and recombinant *C. acetobutylicum* when the subcutaneous tumors reach a diameter of between approximately 0.5 and 1 cm. As a function of time after injection, mice were sacrificed and their tumors removed.

Homogenates of the tumors were prepared, extracts run on a nondenaturing gel and the amount of nitroreductase quantitated by Western blot. Homogenates of normal tissue showed no detectable nitroreductase protein.

D. In vivo Efficacy Studies

In vivo studies with three different transplanted mouse tumors, EMT6, SCCVII and RIF1 tumors and with human colon carcinoma HT29 transplanted into immune-deficient SCID mice were performed. Tumors were injected with spores of control and recombinant *C. acetobutylicum* when the subcutaneous tumors reach a diameter of between approximately 0.5 and 1 cm.

CB1954 was injected into the tumor-bearing mice at different times during the growth of the *C. acetobutylicum* and the response of the tumor was measured by counting the total clonogenic cells per tumor 24 hrs after treatment and by regrowth delay. Upon analysis, it was observed that the level of viable *clostridia* in the tumors were approximately $10^5$ to $10^6$ bacteria per gram of tumor.

Example 2

Expression of Cytosine Deaminase in *Clostridium* spp

A. Vector Construction

A plasmid vector designated pCD540F was constructed as illustrated in FIGS. 7–9. The pMTL500F plasmid described in Example 1 (FIG. 4) was modified by replacing the pAMβ1-derived origin of replication with a replicon derived from the *Clostridium butyricum* plasmid pCB012 (Minton, N. P. et al.) Plasmid pMTL540F was constructed in an analogous fashion to pMTL500F. First, a similar plasmid to pMTL500E (FIG. 4) was made, designated pMTL540E and shown in FIG. 7, by inserting a blunt-ended 1.53 Kb LspI-HindIII fragment from pCB102 into the NheI site, similarly blunt-ended, of the replicon cloning vector pMTL20E (Swinfield et al.). The lac promoter of pMTL540E was then replaced with the promoter of the ferrodoxin (Fd) gene by combining a 3.64 Kb Bg1I fragment from pMTL540E with a 1.871 Kb Bg1I fragment isolated from pMTL500F, as shown in FIG. 8. The resulting plasmid was designated pMTL540F.

Expression of heterologous genes in pMTL540F expression vectors has been found to be optimal when the gene is inserted in at the Nde 1 site of the multiple cloning site (MCS), which is immediately adjacent to the promoter. Since the *E. coli* cytosine deaminase gene contains an internal Nde 1 site, in constructing an expression vector for expression of cytosine deaminase in *Clostridium* spp. the forward primer was designed to contain the Ase 1 restriction site, which generates ends complimentary to those produced by Nde 1. The reverse primer contained a restriction site for Xba 1, allowing directional cloning of the PCR product. The gene encoding cytosine deaminase was amplified from HB101 *E. coli* genomic DNA by PCR and a product of the predicted size was gel-purified, digested with Ase 1 and Xba 1, and ligated to Nde 1/Xba 1 digested vector DNA, as further described in Austin et al., 1993 and Minton et al., 1981. Ligation products were transformed into competent GBE180 *E. coli* and plasmid minipreps performed by a standard procedures. The absence of PCR-induced mutations in the CD gene was confirmed by sequencing prior to large-scale plasmid preparation. The vector containing the cytosine deaminase gene, pCD540FT, is shown in FIG. 9 and is abbreviated in some Figs. as "pCD."

B. Transformation of *C. sporogenes*

*C. sporogenes* was transformed with the pCD540FT vector comprising the coding sequence *E. coli*-derived cytosine deaminase (CD) as follows.

A broth, referred to as "TPGY" broth, was prepared from the following components, with balance water.

| | | |
|---|---|---|
| trypticase peptone | 2% | 20 g/l |
| peptone | 0.5% | 5 g/l |
| glucose | 0.1% | 1 g/l |
| yeast extract | 0.5% | 5 g/l |
| cysteine HCl | 0.1% | 1 g/l |

TPGY agar was prepared with the same components as the TPGY broth, with the addition of 2% agar (20 g/l).

An electroporation buffer was prepared by mixing 10% polyethylene glycol (MW 8,000) containing 1 mg/ml polyanetholesulfonic acid in water.

All broths, buffers and other media were equilibrated to anaerobic conditions prior to transformation, i.e., at least 24 hours before transformation.

An isolate colony of *C. sporogenes* was selected and restreaked onto a fresh TPGY agar plate two days before transformation. One day before transformation, a single colony from the freshly restreaked plate was inoculated into TPGY broth. Serial dilutions (up to $10^5$ times dilution) in 5 ml volumes of TPGY broth were prepared and incubated overnight. Then, 3 ml of culture from the lowest dilution having discernible cell growth was used to inoculate 300 ml (1:100 dilution) of fresh TPGY broth in an airtight centrifuge bottle. The inoculated broth was incubated (typically for 2.5–3 hours) until the midlog phase of growth was reached, as evidenced by spectrophotometric evaluation at 600 nm of the broth for a peak OD of 0.7–0.8.

The culture bottle containing the bacterial cells was tightly capped closed and removed from the hypoxic chamber into an ice bath for at least 10 minutes before centrifugation. The bacterial culture was kept as cold as possible, but not frozen, until electroporation.

For the electroporation, a container filled with dry ice was placed in the hypoxic chamber. The following solutions were placed on support racks along one side of the dry-ice filled container: (i) a solution containing the pCD540FT plasmid vector, (ii) a solution of aurintricarboxylic acid, and (iii) 50 ml centrifuge tubes of the electroporation buffer. Electroporation curvets were also placed in the dry-ice filled container on a support rack.

Just prior to electroporation, the bacterial culture in the culture bottle was centrifuged (6,000 g for 10 minutes) and the cells were harvested and then washed in 10 ml cold electroporation buffer. The washed cells were again harvested by centrifugation (6,000 g for 10 minutes) and then resuspended in 3 ml cold electroporation buffer additionally containing a DNAase inhibitor, aurintricarboxylic acid at 0.1 mg/ml (diluted from stock solution at 100 mg/ml).

Into a 0.2 cm inter-electrode distance curvet, 1–5 μg of cold DNA plasmid vector pCD540FT was added along with 0.4 ml of solution containing the bacterial cells in the DNAase inhibitor-containing buffer. The vector-cell solution in the curvet was pulsed once at 1.25 kV, 25 μFD, 100 ohms and maintained at the cold temperature for an additional 4 minutes.

The pulsed cells were transferred into 4.6 ml TPGY broth prewarmed to about 37° C. containing 25 mM $MgCl_2$ (diluted from 2.5 M stock solution) and incubated for 4 hours. The cell culture was then divided into 5 separate microfuge tubes, each containing 1 ml cell culture. The cells were harvested by centrifugation with a compact microcentrifuge placed inside the hypoxic chamber at 5,600 g for 4 minutes. The cell pellet was resuspended in 100 μl of TPGY broth prewarmed to about 37° C. 100 μl aliquots of the broth containing the cells were plated onto TPGY agar containing 10 μg/ml erythromycin. The plates were incubated for four days.

C. In vitro Activity of Cytosine Deaminase from *C. Sporogenes*

Western blot analysis of cytosine deaminase protein expression in cell lysates of transformed *C. sporogenes* ("*C. sporogenes* w/pCD"), wild-type *C. sporogenes*, and *E. coli* transformed with the same vector ("*E. coli* w/pCD") was performed. The results are shown in FIG. 10.

Conversion of nontoxic 5-fluorocytosine to toxic 5-fluorouracil by the cytosine deaminase-transformed *C. sporogenes* was evaluated by monitoring the growth inhibition of SCCVII cells incubated with 5-FC alone, 5-FU alone, or the addition of cell extract from recombinant *C. sporogenes* added to the culture. The results are shown in FIG. 11.

D. In vivo Expression of Cytosine Deaminase and Antitumor Activity

The expression and activity of cytosine deaminase was evaluated in SCCVII tumor-bearing mice as follows. Tumor-bearing animals were injected intraveneously (iv) with $10^8$ spores of recombinant *C. sporogenes*, and 7 and 14 days later the tumors were excised and samples prepared for immunoblot analysis of cytosine deaminase and for cytosine deaminase activity in vitro as judged by the ability to convert 5-fluorocytosine to a more toxic product. The results are shown in FIG. 12.

In another study, SCCVII tumor-bearing mice were injected iv with $10^8$ spores of recombinant *C. sporogenes* when the tumors were approximately 100 mg in size. Seven days after injection, the tumor, brain, heart, lung, liver, kidney, and spleen tissues were removed for immunoblot analysis. 100 μg of cell extract from each of the tissues was loaded on gels and subjected to immunoblot analysis following gel electrophoresis. As controls, 1 μg and 20 μg of cell extracts from cytosine deaminase-transformed *E. coli* and *C. sporogenes*, respectively, were loaded onto the gel. The results are shown in FIG. 12.

Figure 14:
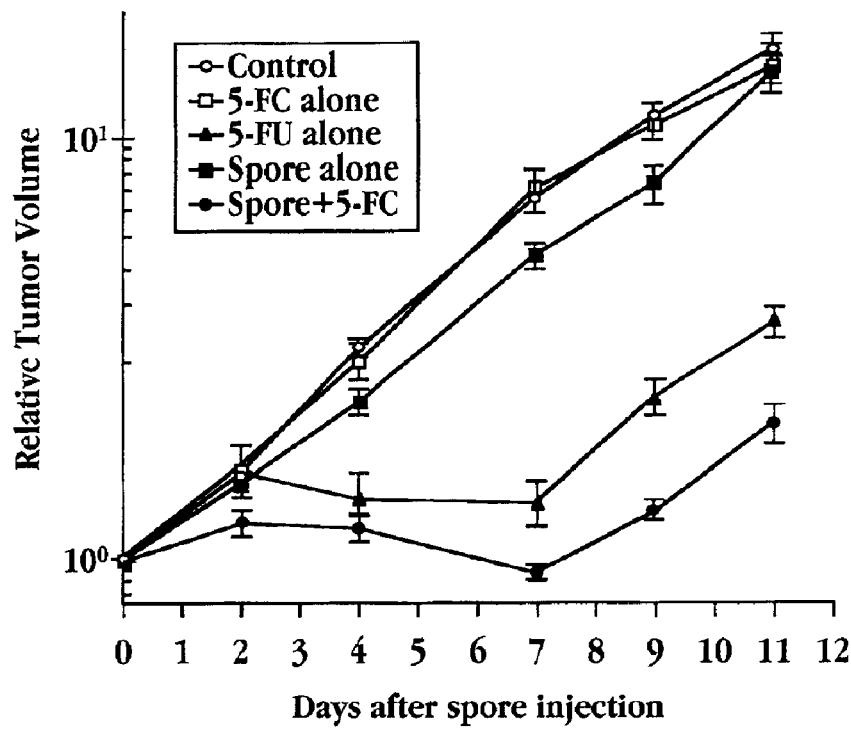
FIG. 14 is a plot of relative tumor volume as a function of days after injection of $10^8$ spores of recombinant cytosine deaminase-transformed C. sporogenes on day 0 and treated with saline (control; open circles), 5-FC (open squares), 5-FU (closed triangles), recombinant spores (closed squares), or recombinant spores plus 5-FC (closed circles). The data reflects the analysis of five mice per group reported as mean+standard error of the mean (SEM).

In another study, the ability of recombinant CD-expressing *C. sporogenes* to produce sufficient conversion of 5-FC to 5-FU in vivo to produce antitumor activity was also evaluated. Groups of tumor-bearing mice with an average tumor size of 150 mg were injected with saline, 5-FC (500 mg/kg 5 times per week for 2 weeks), a maximum tolerated dose of 5-FU alone (16.6 mg/kg daily 5 days per week for 2 weeks), recombinant spores alone on day 0, or recombinant spores one day prior to daily injections of 5-FC. The results are shown in FIG. 14.

Example 3

Expression of the β-glucuronidase Gene (uidA) in *C. acetobutylicum*

Oligonucleotide primers, based on the published sequence, were utilized to amplify a fragment carrying the β-glucuronidase gene from *E. coli* K12 (Jefferson et al., 1986). One of the PCR primers employed created an NdeI site 'over' the uidA start codon, to facilitate insertion of the gene into pMTL500F, described in Example 1 and shown in FIG. 4, resulting in a modified form of the pMTL500F vector comprising the coding sequence for β-glucuronidase.

β-glucuronidase has to be exported out of the clostridial cell in order to be active. To achieve this, the uidA gene was constructed with a 5' signal sequence to promote secretion of the translated protein by the classical signal peptide route (Bosslet et al., 1992). Two signal sequences were employed: (1) the *Clostridium thermocellum* celA gene (Beguin et al., 1985); and (2) the staphylococcal protein A gene (Shuttleworth et al., 1987). The 5'-end of the lacZ' gene of pMTL500F (that residing between the NdeI site and polylinker region) was replaced with DNA specifying the two signal sequences. The resulting plasmid was transformed into *C. acetobutylicum* NCIMB 8052 by electroporation.

What is claimed is:

1. A composition comprising an obligately anaerobic bacteria of the genus *Clostridium* transformed with a recombinant expression vector including the coding sequence for an enzyme capable of catalyzing the conversion of a prodrug into a chemotherapeutic agent, wherein said bacteria have the ability to germinate in a tumor.

2. An obligately anaerobic *Clostridium* bacterial composition, comprising a coding sequence for an enzyme capable of catalyzing the conversion of a prodrug into a chemotherapeutic agent, wherein said bacteria have the ability to germinate in a tumor.

3. The composition according to claim 1, wherein the enzyme is selected from the group consisting of cytosine deaminase, nitroreductase, β-glucuronidase, and alkaline phosphatase.

4. The composition according to claim 1, wherein the prodrug is selected from the group consisting of a glucuronide, a glucuronide of epirubicin, 5-fluorocytosine, CB1954, 4-hydroxycyclophosphamide, hydroxyanaline mustard, and 5-fluorouracil.

5. The composition according to claim 1, wherein the prodrug is 5-fluorocytosine.

6. The composition according to claim 1, wherein the enzyme is cytosine deaminase.

7. The composition according to claim 2, wherein the enzyme is selected from the group consisting of cytosine deaminase, nitroreductase, β-glucuronidase, and alkaline phosphatase.

8. The composition according to claim 2, wherein the prodrug is selected from the group consisting of a glucuronide, a glucuronide of epirubicin, 5-fluorocytosine, CB1954, 4-hydroxycyclophosphamide, hydroxyanaline mustard, and 5-fluorouracil.

9. The composition according to claim 2, wherein the prodrug is 5-fluorocytosine.

10. The composition according to claim 2, wherein the enzyme is cytosine deaminase.

11. A composition comprising *Clostridium* bacteria genetically engineered to express an enzyme capable of converting a prodrug into a chemotherapeutic agent, wherein said bacteria have the ability to germinate in a tumor.

12. The composition according to claim 11, wherein the enzyme is selected from the group consisting of cytosine deaminase, nitroreductase, β-glucuronidase, and alkaline phosphatase.

13. The composition according to claim 11, wherein the prodrug is selected from the group consisting of a glucuronide, a glucuronide of epirubicin, 5-fluorocytosine, CB1954, 4-hydroxycyclophosphamide, hydroxyanaline mustard, and 5-fluorouracil.

14. The composition according to claim 11, wherein the prodrug is 5-fluorocytosine.

15. The composition according to claim 11, wherein the enzyme is cytosine deaminase.

16. The composition according to claim 11, wherein the bacteria is *Clostridium sporogenes*.

17. The composition according to claim 1, wherein the bacteria is *Clostridium sporogenes*.

18. The composition according to claim 17, wherein the enzyme is selected from the group consisting of cytosine deaminase, nitroreductase, β-glucuronidase, β-galactosidase, carboxypeptidase, alkaline phosphatase and β-lactamase.

19. The composition according to claim 17, wherein the prodrug is selected from the group consisting of a glucuronide conjugate of epirubicin, a glucuronide conjugate of doxorubicin, 5-fluorocytosine, CB1954, 4-hydroxycyclophosphamide, hydroxyanaline mustard, etoposide phosphate, doxorubicin phosphate, mitomycin C phosphate, and 5-fluorocytosine.

20. The composition according to claim 19, wherein the prodrug is 5-fluorocytosine.

21. The composition according to claim 17, wherein the enzyme is cytosine deaminase.

22. The obligately anaerobic bacterial composition according to claim 2, wherein the bacteria is *Clostridium sporogenes*.

23. The obligately anaerobic bacterial composition according to claim 2, wherein the enzyme is selected from the group consisting of cytosine deaminase, nitroreductase, β-glucuronidase, β-galactosidase, carboxypeptidase, alkaline phosphatase, and β-lactamase.

24. The anaerobic bacterial composition according to claim 2, wherein the prodrug is selected from the group consisting of a glucuronide conjugate of epirubicin, a glucuronide conjugate of doxorubicin, 5-fluorocytosine, CB1954, 4-hydroxycyclophosphamide, hydroxyanaline mustard, etoposide phosphate, doxorubicin phosphate, mitomycin C phosphate, and 5-fluorocytosine.

25. The anaerobic bacterial composition according to claim 24, wherein the prodrug is 5-fluorocytosine.

26. The anaerobic bacterial composition according to claim 24, wherein the enzyme is cytosine deaminase.

* * * * *

UNITED STATES PATENT AND TRADEMARK OFFICE
CERTIFICATE OF CORRECTION

PATENT NO. : 6,984,513 B2  
DATED : January 10, 2006  
INVENTOR(S) : John Martin Brown et al.

It is certified that error appears in the above-identified patent and that said Letters Patent is hereby corrected as shown below:

<u>Column 1,</u>
Line 17, insert the following paragraph:
    -- This work was supported in part by The National Institutes of Health Grant CA 15201. Accordingly the United States government may have certain rights in this invention. --.

Signed and Sealed this

Twenty-eighth Day of March, 2006

JON W. DUDAS
*Director of the United States Patent and Trademark Office*

SEQUENCE LISTING

<160> NUMBER OF SEQ ID NOS: 1

<210> SEQ ID NO 1
<211> LENGTH: 206
<212> TYPE: DNA
<213> ORGANISM: Clostridium pasteurianum

<400> SEQUENCE: 1

```
gaattccccg gatcgagata gtatatgatg catattcttt aaatatagat aaagttatag      60
aagcaataga agatttagga tttactgtaa tataaattac acttttaaaa agtttaaaaa     120
catgatacaa taagttatgg ttggaattgt tatccgctca caattccaac ttatgattaa     180
aattttaagg aggtgtattt catatg                                          206
```